(12) United States Patent
Carlius et al.

(10) Patent No.: US 9,783,565 B2
(45) Date of Patent: Oct. 10, 2017

(54) LIQUEFACTION OF BIOMASS AT LOW PH

(71) Applicant: Renmatix, Inc., King of Prussia, PA (US)

(72) Inventors: Anders Carlius, Lund (SE); Andreas Gram, Höör (SE); Corinne Granath, Eslöv (SE); Haukur Jóhannesson, Lund (SE); Göran Karlsson, Helsingborg (SE)

(73) Assignee: Renmatix, Inc., King of Prussia, PA (US)

( * ) Notice: Subject to any disclaimer, the term of this patent is extended or adjusted under 35 U.S.C. 154(b) by 0 days.

(21) Appl. No.: 14/356,388

(22) PCT Filed: Nov. 8, 2012

(86) PCT No.: PCT/SE2012/051215
§ 371 (c)(1),
(2) Date: May 5, 2014

(87) PCT Pub. No.: WO2013/070160
PCT Pub. Date: May 16, 2013

(65) Prior Publication Data
US 2014/0323716 A1 Oct. 30, 2014

Related U.S. Application Data

(60) Provisional application No. 61/557,029, filed on Nov. 8, 2011, provisional application No. 61/557,026, filed on Nov. 8, 2011, provisional application No. 61/556,973, filed on Nov. 8, 2011, provisional application No. 61/556,969, filed on Nov. 8, 2011.

(30) Foreign Application Priority Data

Nov. 8, 2011 (SE) .................... 1151046
Nov. 8, 2011 (SE) .................... 1151047
Nov. 8, 2011 (SE) .................... 1151048
Nov. 8, 2011 (SE) .................... 1151049

(51) Int. Cl.
| | | |
|---|---|---|
| C07H 1/00 | (2006.01) |
| C07H 3/02 | (2006.01) |
| C07H 3/10 | (2006.01) |
| B01D 11/02 | (2006.01) |
| C08H 8/00 | (2010.01) |
| C13K 1/02 | (2006.01) |
| D21C 3/00 | (2006.01) |
| D21C 5/02 | (2006.01) |
| C08H 7/00 | (2011.01) |
| D21C 3/04 | (2006.01) |
| D21C 9/00 | (2006.01) |

(52) U.S. Cl.
CPC ........... *C07H 1/00* (2013.01); *B01D 11/0203* (2013.01); *C07H 3/02* (2013.01); *C07H 3/10* (2013.01); *C08H 6/00* (2013.01); *C08H 8/00* (2013.01); *C13K 1/02* (2013.01); *D21C 3/003* (2013.01); *D21C 3/04* (2013.01); *D21C 5/02* (2013.01); *D21C 9/007* (2013.01); *C12P 2201/00* (2013.01); *Y02P 20/544* (2015.11); *Y02W 30/648* (2015.05)

(58) Field of Classification Search
CPC ........................................................ C07H 1/00
See application file for complete search history.

(56) References Cited

U.S. PATENT DOCUMENTS

| | | | |
|---|---|---|---|
| 691,671 A | 1/1902 | Sjoo et al. | |
| 3,413,189 A | 11/1968 | Backlund | |
| 3,766,077 A * | 10/1973 | Hwa et al. | C02F 5/10 134/2 |
| 3,985,659 A * | 10/1976 | Felicetta | C09K 8/24 507/108 |
| 4,175,066 A * | 11/1979 | Shibazaki | B01F 17/0028 210/701 |
| 4,196,094 A | 4/1980 | Johnson et al. | 134/2 |

(Continued)

FOREIGN PATENT DOCUMENTS

| | | |
|---|---|---|
| CA | 2660990 A1 | 8/2009 |
| CN | 101613377 A | 12/2009 |

(Continued)

OTHER PUBLICATIONS

Hydrothermal liquefaction of biomass: A review of subcritical water technologies Saqib Sohail Toor et al. Energy, vol. 36, pp. 2328-2342, available online Mar. 31, 2011*

(Continued)

*Primary Examiner* — Douglas B Call
*Assistant Examiner* — Douglas Call
(74) *Attorney, Agent, or Firm* — Travis B. Gasa; Andrew G. Bunn; Ballard Spahr LLP (57) ABSTRACT

The present invention relates to regulation of the p H of a liquefaction process. Presented is a method for treatment of a biomass feedstock wherein the biomass feedstock is subjected to liquefaction, at a p H of at most 4, by treatment with hot compressed liquid water (HCW) at subcritical and/or supercritical conditions to improve the conversion efficiency. The present invention is also directed to quenching of a liquefaction process according to above, preventing, minimizing or eliminating clogging and/or fouling of sticky biomass components in process equipment during processing as according to above, and to the use of additives in a biomass liquefaction process.

29 Claims, 2 Drawing Sheets

(56) References Cited

U.S. PATENT DOCUMENTS

| | | | |
|---|---|---|---|
| 4,342,831 A | 8/1982 | Faber et al. | |
| 4,461,648 A | 7/1984 | Foody | |
| 4,941,944 A | 7/1990 | Chang | 162/19 |
| 5,041,192 A | 8/1991 | Sunol et al. | 162/63 |
| 5,043,432 A | 8/1991 | Dilling | |
| 5,411,594 A | 5/1995 | Brelsford | |
| 6,022,419 A | 2/2000 | Torget et al. | |
| 6,228,177 B1 | 5/2001 | Torget | |
| 6,409,841 B1 | 6/2002 | Lombard | 127/37 |
| 6,419,788 B1 | 7/2002 | Wingerson | 162/14 |
| 8,317,928 B1* | 11/2012 | Iyer | C04B 24/18 127/57 |
| 2002/0148575 A1 | 10/2002 | Wingerson | |
| 2004/0094144 A1 | 5/2004 | Ikegami et al. | |
| 2005/0039599 A1 | 2/2005 | Johnson et al. | |
| 2006/0188965 A1 | 8/2006 | Wyman et al. | |
| 2006/0286628 A1 | 12/2006 | Everett et al. | |
| 2007/0267008 A1* | 11/2007 | Funazukuri | C08B 15/02 127/41 |
| 2008/0029233 A1 | 2/2008 | Wingerson et al. | |
| 2008/0044877 A1 | 2/2008 | Penttila et al. | |
| 2008/0057555 A1 | 3/2008 | Nguyen | |
| 2008/0064906 A1* | 3/2008 | Foody | C12P 7/10 585/242 |
| 2008/0121359 A1* | 5/2008 | Holtzapple | C05F 5/002 162/90 |
| 2010/0043782 A1 | 2/2010 | Kilambi et al. | |
| 2010/0048884 A1* | 2/2010 | Kilambi | C07H 1/08 536/56 |
| 2010/0048924 A1 | 2/2010 | Kilambi | 549/489 |
| 2010/0063271 A1 | 3/2010 | Allan et al. | |
| 2010/0069626 A1 | 3/2010 | Kilambi | 536/56 |
| 2010/0184176 A1 | 7/2010 | Ishida et al. | |
| 2010/0313882 A1 | 12/2010 | Dottori et al. | |
| 2011/0179703 A1* | 7/2011 | Gupta | C10G 1/02 44/621 |
| 2011/0300617 A1 | 12/2011 | Genta | |
| 2012/0282465 A1 | 11/2012 | Kadam et al. | |
| 2013/0171709 A1 | 7/2013 | Kusuda et al. | |
| 2014/0030524 A1* | 1/2014 | Kadam | C08H 6/00 428/402 |
| 2016/0053337 A1* | 2/2016 | Ekman | C13K 1/02 127/37 |

FOREIGN PATENT DOCUMENTS

| | | |
|---|---|---|
| CN | 101709227 A | 5/2010 |
| CN | 101851688 A | 10/2010 |
| CN | 102071040 | 5/2011 |
| CN | 102071040 A | 5/2011 |
| EP | 1 076 042 A1 | 2/2001 |
| EP | 1076042 A1 | 2/2001 |
| EP | 1561730 A1 | 8/2005 |
| EP | 1716920 A1 | 11/2006 |
| EP | 2075347 A1 | 7/2009 |
| EP | 13784501 | 4/2013 |
| GB | 2100282 A | 12/1982 |
| JP | 2001262162 A | 9/2001 |
| JP | 2001-300486 A | 10/2001 |
| JP | 2005/081332 A | 3/2005 |
| JP | 2007/111673 A | 5/2007 |
| JP | 2008-142599 | 6/2008 |
| JP | 2009/178657 A | 8/2009 |
| JP | 2009/183806 A | 8/2009 |
| JP | 4699566 | 6/2011 |
| JP | 4699566 B1 | 6/2011 |
| KR | 100904561 B1 | 6/2009 |
| SE | 1150059-2 | 1/2011 |
| WO | WO 9002836 | 3/1990 |
| WO | WO 01/88258 | 11/2001 |
| WO | WO-2006/0128304 A1 | 12/2006 |
| WO | WO 2007/128798 | 11/2007 |
| WO | 2008/121043 A1 | 10/2008 |
| WO | WO 2008/121043 | 10/2008 |
| WO | 2011/091044 A1 | 7/2011 |
| WO | WO 2011/091044 * | 7/2011 |
| WO | WO 2011/091044 A1 | 7/2011 |
| WO | WO 2011/094859 * | 8/2011 |
| WO | WO-2012/042840 A1 | 4/2012 |
| WO | 2012/060767 A1 | 5/2012 |
| WO | WO 2012/060767 * | 5/2012 |
| WO | WO 2012/141652 | 10/2012 |
| WO | WO-2013/013318 A1 | 1/2013 |
| WO | WO 2013/165308 | 11/2013 |
| WO | WO 2014/074066 | 5/2014 |

OTHER PUBLICATIONS

Glucose reactions with acid and base catalysts in hot compressed water at 473K. Masaru Watanabe et al. Carbohydrate Research, v 340, pp. 1925-1930, 2005.*

International Type Search Report mailed Apr. 19, 2012 for National Application No. 1151049-2, which was filed Nov. 8, 2012 (Applicant—Reac Fuel Ab//1st Named Inventor—Granath) (5 pages).

International Type Search Report mailed May 15, 2012 for National Application No. 1151048-4, which was filed Nov. 8, 2012 (Applicant—Reac Fuel Ab//1st Named Inventor—Granath) (5 pages).

International Type Search Report mailed May 3, 2012 for National Application No. 1151047-6, which was filed Nov. 8, 2012 (Applicant—Reac Fuel Ab//1st Named Inventor—Granath) (5 pages).

International Type Search Report mailed May 16, 2012 for National Application No. 1151046-8, which was filed Nov. 8, 2012 (Applicant—Reac Fuel Ab//1st Named Inventor—Granath) (7 pages).

Swedish Office Action mailed Apr. 19, 2012 for National Application No. 1151049-2, which was filed Nov. 8, 2012 (Applicant—Reac Fuel Ab//1st Named Inventor—Granath) (10 pages).

Swedish Office Action mailed May 16, 2012 for National Application No. 1151046-8, which was filed Nov. 8, 2012 (Applicant—Reac Fuel Ab//1st Named Inventor—Granath) (10 pages).

Swedish Office Action mailed May 3, 2012 for National Application No. 1151047-6, which was filed Nov. 8, 2012 (Applicant—Reac Fuel Ab//1st Named Inventor—Granath) (10 pages).

Swedish Office Action mailed May 15, 2012 for National Application No. 1151048-4, which was filed Nov. 8, 2012 (Applicant—Reac Fuel Ab//1st Named Inventor—Granath) (8 pages).

International Search Report mailed Feb. 19, 2013, issued in corresponding International Application No. PCT/SE2012/051215, filed Nov. 8, 2012, 5 pages.

Oh, H., et al., "Evaluation of PAC Behavior and Fouling Formation in an Integrated PAC-UF Membrane for Surface Water Treatment," Desalination 192(1-3):54-62, May 2006.

Oh, H. et al; Evaluation of PAC behavior and fouling formation in an integrated PAC-UF membrane for surface water treatment; Desalination 198 (1-3), pp. 54-62.

Written Opinion and International Search Report mailed Jul. 7, 2012 for Application No. PCT/SE2012/051215, which was filed Nov. 8, 2012 and published as WO 2013/070160 (Applicant—Reac Fuel Ab//1st Named Inventor—Carlius) (12 pages).

International Preliminary Report on Patentability issued May 13, 2014 for Application No. PCT/SE2012/051215, which was filed Nov. 8, 2012 and published as WO 2013/070160 (Applicant—Reac Fuel Ab//1st Named Inventor—Carlius) (8 pages).

Hendriks, et al., "Pretreatments to enhance the digestibility of lignocellulosic biomass", Bioresource Technology, vol. 100, (2009) (pp. 10-18).

Non-Final Office Action issued on Dec. 3, 2015 for U.S. Appl. No. 14/441,427, filed May 7, 2015 and published as US-2015-0292049-A on Oct. 15, 2015 (Applicant—Renmatix, Inc. // Inventor—Carlius, et al.) (19 pages).

Non-Final Office Action issued on Nov. 9, 2015 for U.S. Appl. No. 14/397,805, filed Oct. 29, 2014 and published as US-2015-0122245-A1 on May 7, 2015 (Applicant—Renmatix, Inc. // Inventor—Johannesson, et al.) (18 pages).

First Office Action issued by the State Intellectual Property Office of the People's Republic of China for application CN 201380022618.1 (Applicant—Renmatix, Inc.) (Original—16 pages // Translation—6 pages).

(56) References Cited

OTHER PUBLICATIONS

Final Office Action issued on Mar. 25, 2016 for U.S. Appl. No. 14/397,805, filed Oct. 29, 2014 and published as US-2015-0122245-A1 on May 7, 2015 (Applicant—Renmatix, Inc. // Inventor—Johannesson, et al.) (21 pages).
Chen et al., Transformation of Lignocellulose to Produce Fuel Ethanol, "Straw Resource High Ecological Value Theory and Application", Beijing Chemical Industry Press, Sep. 2006, 1st Edition, pp. 166-170, Section 4.3.1.2 and Section 4.3.1.4 (Original—6 pages // English Language Abstract and Table of Contents—3 pages).
Extended European Search Report dated Aug. 29, 2014 for application EP 12771085.3, filed Apr. 13, 2012 and published as EP 2697380 on Feb. 19, 2014 (Applicant—Renmatix, Inc.) (7 pages).
Extended European Search Report dated Jan. 8, 2016 for application EP 13784501.2, filed Apr. 30, 2013 and published as EP 2844777 on Mar. 11, 2015 (Applicant—Renmatix, Inc. // Inventor—Johannesson, et al.) (8 pages).
Allen, S.G. et al., Fractionation of Sugar Cane with Hot, Compressed, Liquid Water. Ind Eng Chem Res. 1996; 35(8): 2709-15.
Ehara, K. et al., A Comparative Study on Chemical Conversion of Cellulose Between the Batch-type and Flow-type Systems in Supercritical Water. Cellulose. 2002; 9(3-4):301-11.; abstract; figure 1; table 1.
Hashaikeh, R. et al., Hydrothermal Dissolution of Willow in Hot Compressed Water as a Model for Biomass Conversion. Fuel. 2007; 86(10-11): 1614-22.
Holladay, J.E. et al., Top Value-Added Chemicals from Biomass vol. II-Results of Screening for Potential Candidates from Biorefinery Lignin. Dept Energy (87 pages) (2007).
Kumagai, S. et al., Fractionation and Solubilization of Cellulose in Rice Hulls by Hot-Compressed Water Treatment, and Production of Glucose from the Solubilized Products by Enzymatic Saccharification. Kagaku Kogaku Ronbunshu 2008; 34(4):458-62 (Abstract Only).
Liu, C. et al., Partial Flow of Compressed-Hot Water through Corn Stover to Enhance Hemicellulose Sugar Recovery and Enzymatic Digestibility of Cellulose. Bioresour Technol. 2005; 96(18): 1978-85; paragraphs 2.2, 3.4, table 1.
Matsunaga, M. et al., Super-Rapid Chemical Conversion of Sugi [Cryptomeria japonica] Wood by Supercritical and Subcritical Water Treatment. Mokuzai Gakkaishi. 2004; 50(5):325-32 (Abstract Only).
Mosier et al., Features of Promising Technologies for Pretreatment of Lignocellulosic Biomass. Bioresour Technol. 2005; 96(6): 673-86.
Phaiboonsilpa, N. et al., Effect of Acetic Acid Addition on Chemical Conversion of Woods as Treated by Semi-Flow Hot-Compressed Water. Holzforschung. 2011; 65(5): 667-72.
Phaiboonsilpa, N. et al., Two-Step Hydrolysis of Nipa (Nypa fruticans) Frond as Treated by Semi-Flow Hot-Compressed Water. Holzforschung. 2011; 65(5): 659-66.
Phaiboonsilpa, N. et al., Two-step hydrolysis of Japanese Cedar as Treated by Semi-Flow Hot-Compressed Water. J Wood Sci. 2010; 56(4):331-8.
Sakaki, T. et al., Decomposition of Cellulose in Near-Critical Water and Fermentability of the Products. Energy Fuels. 1996; 10: 684-8.
Yoshida, H. et al., Efficient, High-Speed Methane Fermentation for Sewage Sludge Using Subcritical Water Hydrolysis as Pretreatment. Bioresour Technol. 2009; 100(12):2933-9.
Yu, Y. et al., Some Recent Advances in Hydrolysis of Biomass in Hot-Compressed Water and Its Comparisons with Other Hydrolysis Methods. Energy Fuels. 2008; 22(1): 46-60.
Extended European Search Report dated Jun. 7, 2017 for application 11838318.1, which was filed on Oct. 28, 2011 and published as 2635713 on Sep. 11, 2013 (Inventor—Ekman et al.; Applicant—Reac Fuel Ab, Inc.) (8 pages).
International Search Report and Written Opinion dated Jan. 19, 2012 by the International Searching Authority for application PCT/SE2011/051292, which was filed on Oct. 28, 2011 and published as WO 2012/060767 on May 10, 2012 (Inventor—Eckman; Applicant—Reac Fuel Ab) (13 pages).
Office Action dated Aug. 1, 2016 by the SIPO for Chinese Patent application 201280054929.1, which was filed on Nov. 8, 2012 (Inventor—Carlius et al.; Applicant—Reac Fuel AB) (8 pages).
Extended European Search Report dated Jun. 29, 2015 for application 112847440.0, which was filed on Nov. 8, 2012 and published as 2776591 on Sep. 17, 2014 (Inventor—Carilus et al.; Applicant—Reac Fuel AB) (7 pages).
International Search Report mailed by the International Searching Authority dated Aug. 27, 2013 for application PCT/SE2013/050478, filed Apr. 30, 2013, and published as WO 2013/165308 on Nov. 7, 2013 (Inventor—Jóhannesson et al.; Applicant—Reach Fuel AB) (5 pages).
Written Opinion mailed by the International Searching Authority dated Aug. 27, 2013 for application PCT/SE2013/050478, filed Apr. 30, 2013, and published as WO 2013/165308 on Nov. 7, 2013 (Inventor—Jóhannesson et al.; Applicant—Reac Fuel AB) (6 pages).
International Search Report dated May 7, 2012 by the International Searching Authority for application PCT/SE2013/050406, which was filed on Apr. 13, 2012 and published as WO 2012/141652 on Oct. 18, 2012 (Inventor—Carilus, et al.; Applicant—Reac Fuel AB) (5 pages).
Written Opinion mailed by the International Searching Authority dated May 7, 2012 for application PCT/SE2013/050406, which was filed on Apr. 13, 2012 and published as WO 2012/141652 on Oct. 18, 2012 (Inventor—Carilus, et al.; Applicant—Reac Fuel AB) (5 pages).
Extended European Search Report dated May 25, 2016 for Application No. 13853191.8, which was filed on Nov. 8, 2013 and published as 2917376 on Sep. 16, 2015 (Inventor—Anders Carlius et al) (8 pages).
International Search Report dated May 15, 2014 for application PCT/SE2013/051324, which was filed on Nov. 8, 2013 and published as WO 2014/074066 on May 15, 2014 (Inventor—Carilus, et al.; Applicant—Reac Fuel AB) (5 pages).
Written Opinion dated May 15, 2014 for application PCT/SE2013/051324, which was filed on Nov. 8, 2013 and published as WO 2014/074066 on May 15, 2014 (Inventor—Carilus, et al.; Applicant—Reac Fuel AB) (5 pages).

* cited by examiner

LIQUEFACTION OF BIOMASS AT LOW PH

FIELD OF THE INVENTION

The present invention relates to a process for treatment of biomass at super-critical and/or subcritical conditions.

TECHNICAL BACKGROUND

Different processes for degrading and converting biomass into value-adding compounds are known. Degradation of biomass in sub- or super-critical conditions is known.

WO2011/091044 discloses methods for the continuous treatment of biomass, comprising a pretreatment step, wherein said biomass is contacted with a first supercritical, near-critical, or sub-critical fluid to form a solid matrix and a first liquid fraction; and a hydrolysis step, wherein said solid matrix formed in said pretreatment step is contacted with a second super-critical or near-supercritical fluid to produce a second liquid fraction and an insoluble lignin-containing fraction. According to the processes disclosed in WO2011/091044, water, and carbon dioxide are introduced to the reactors for the degradation. Optionally acid may be added after the first pretreatment step but before a possible separation step and optionally acid may also be used in the second step, the hydrolysis reaction.

Modifications to prior art techniques are needed to improve the efficiency of converting of biomass from renewable resources and/or waste materials to more valuable products. Thus there is a need to optimize the known processes and to increase the output of degraded material.

SUMMARY OF A FIRST ASPECT OF THE INVENTION

The present invention is directed to providing an improved process for treating a biomass material by liquefaction at subcritical and/or supercritical conditions and is given the opportunity to obtain as large output as possible of degraded material and/or control the liquefaction reaction.

The present invention relates to a method for treatment of a biomass feedstock wherein the biomass feedstock is subjected to liquefaction, at a pH of at most 4, by treatment with hot compressed liquid water (HCW) at subcritical and/or supercritical conditions.

According to one specific embodiment, the method also comprises a quenching step. Alternatives of this step are further disclosed below.

Specific embodiments of the invention disclose a pH of 1-4, such as 2-4, or 2.0-3.1 or 2.3-3.1 during the degradation. One specific range of interest is a pH level of 1.2-3.3.

To obtain the desired pH inorganic and/or organic acids may be added to the biomass feedstock before and/or during the liquefaction.

According to the present invention it is preferred to perform the treatment in hot compressed liquid water (HCW) at subcritical conditions and not at supercritical conditions. This depends on several different factors, such as inter alia the possibility of providing an intended product composition, suppressing the energy consumption and upholding a production environment which is more lenient for equipment and people. The preferred environment of a subcritical, and not supercritical, condition is valid for all aspects of the present invention, i.e. also the ones disclosed below.

In an embodiment of the present invention the liquefaction is performed at a temperature of at least 200° C., e.g. in the range of 200-300° C.

In another embodiment the liquefaction is performed at sub-critical conditions implying a temperature of below 374° C., e.g. in the range 220-280° C. According to one specific embodiment, the temperature is in the range of 240-290° C., which seems to be a very efficient temperature range.

In yet another embodiment the liquefaction is performed sequentially in at least two separate reactors, and wherein separation of a liquid phase is performed after each reactor.

In still another embodiment the liquefaction is performed in a continuous flow system.

Further, the liquefaction method may be performed free from any other added solvents besides HCW.

SPECIFIC EMBODIMENTS OF A FIRST ASPECT OF THE INVENTION

Biomass is degraded by the aid of liquefaction using hot compressed liquid water (HCW) at subcritical or supercritical conditions. Improved degradation and a high content of resulting monomers and oligomers are obtained by the method according to the present invention that includes a regulation of the pH before and/or during the liquefaction. By regulating the pH of the thermal degradation process to be in the acidic range and at most 4, the output may be increased considerably. The regulation of the pH also presents an opportunity to lower the reaction temperature of the process and still get a very good output. However, the pH value may not only be used for optimizing the output of a liquefaction it may also be used to control the conversion of organic material during liquefaction. The pH may according to the present invention also be used for quenching a liquefaction of a biomass. As the pH value of the liquefaction is a driver for the degradation of the cellulose and hemicelluloses into oligomers and monomers, increasing the pH value of the solution may function for stopping or at least slowing down a continued detrimental decomposition or degradation. Varying the pH may also be used to adjust the obtained relative fractions of monomers and oligomers in the product solution. The more acidic the conditions are the higher amount of monomers is obtained. During the liquefaction according to the present invention, the pH value of the solution should be at most 4, preferably below 3.5, more preferred below 3, even below 2 and down to 1. Also, a buffer may be added to keep the pH in the desired range. When high enough yields of wanted oligomers and monomers have been obtained and it is hence desirable to avoid a continued decomposition, the pH value may be increased to slow down or quench a continued degradation according to the present invention. According to the present invention, an alkaline liquid could be added so that the pH value is increased, e.g. above 5. Therefore, according to one specific embodiment of the present invention, an alkaline liquid, e.g. sodium and/or potassium hydroxide, may be added to the biomass process flow solution for adjustment of the pH value of the biomass process flow solution from a pH value of maximum 4 before the adjustment and to a pH value of at least 5 after the adjustment. A range of the pH of 5.0-11, may be a suitable level for the pH after quenching or reduction in degradation.

The pH of the material to be thermally treated using hot compressed liquid water (HCW) at subcritical and/or supercritical conditions is at most 4, preferably with in a range of 1-4, such as 1.2-3.3, or 2.0-3.1, 2.3-3.1, 2.5-3.0, 2.5-2.8, 2.55-2.75, or 2.60-2.75.

A pH of at most 4 may be obtained by addition of inorganic or organic acids. Suitable inorganic acids may be chosen from sulfuric acid, sulfonic acid, phosphoric acid, phosphonic acid, nitric acid, nitrous acid, hydrochloric acid, hydrofluoric acid, hydrobromic acid, and hydroiodic acid, or any combination. Suitable organic acids may be chosen from aliphatic carboxylic acids (e.g. acetic acid and formic acid), aromatic carboxylic acids (e.g. benzoic acid and salicylic acid), dicarboxylic acids (e.g. oxalic acid, phthalic acid, sebacic acid, and adipic acid), aliphatic fatty acids (e.g. oleic acid, palmitic acid, and stearic acid), aromatic fatty acids (e.g. phenylstearic acid), and amino acids, or any combination. Also, organic acids may be produced during the liquefaction process, which influences the pH. Also, by using different biomass matrixes, different acids may be formed. Thus, by controlling which type of ingoing biomass materials are used, the type of organic acids formed during the liquefaction may also be controlled. The usage of biomass such as found in trees, grasses, agricultural waste, and waste paper all may influence the production of formed organic acids.

Biomass may be degraded in sequential steps. By subjecting biomass to hot compressed liquid water at subcritical and/or supercritical conditions in different steps the total amount of resulting monomers and oligomers obtained may be increased. Hot compressed liquid water at subcritical and/or supercritical conditions may be injected where the reaction takes place, e.g. a reactor, creating subcritical and/or supercritical conditions in the reactor, or water present in such a reactor may be brought up to subcritical and/or supercritical conditions resulting in hot compressed liquid water. Preferably the sequential steps have an increasing temperature for each step of the treatment. The present process is not limited to a specific number of liquefaction steps, i.e. one, two, three etc. liquefaction steps may be performed.

After a first liquefaction the water soluble and liquid materials may be separated from the remaining solids. In the fraction with the water soluble and liquid materials removed from the solids there are the monomers and oligomers of sugars obtained from the degradation of the biomass. The formed organic acids obtained from the liquefaction in the sugar solution may be further processed so that the organic acids are separated from the sugar solution. The organic acids may then be reused in the process or be used as a component for other processes.

The remaining solids after the first liquefaction may be subjected to further liquefactions. A second liquefaction is then preferably preformed at a higher temperature. If a second or more liquefactions are used the pH is preferably kept within the ranges disclosed above and may not necessarily be identical for the subsequent treatments.

As notable from above, the liquefaction may be performed in "sub- and/or super-critical condition" which implies that both of these conditions are possible as well as a combination where one first liquefaction step first may be performed in e.g. a sub-critical condition and a second liquefaction step mat be performed in e.g. a super-critical condition. In relation to the above stated it should be mentioned that the liquefaction according to the present invention preferably is performed in a sub-critical condition for HCW, but above 200° C. Therefore, according to one specific embodiment of the present invention, the liquefaction is performed in a temperature of at least 200° C.

A biomass comprises cellulose, hemicelluloses and possibly lignin. The biomass may be lignocellulosic biomass which mainly comprises cellulose, hemicelluloses and lignin. For dissolving hemicellulose effectively, the temperature should preferably be held at least 200° C., preferably at least 230° C., preferably at least 250° C. As such these temperatures may be seen as preferred minimum levels for the liquefaction according to the present invention.

For dissolving cellulose, the temperature should be at least 260° C. Therefore, according to one specific embodiment of the present invention the liquefaction is performed in a temperature of at least 260° C. Also the reaction time is an important parameter. According to the present invention, the reaction time should be held short, irrespective if e.g. a semi-batch or a continuous flow system is used for the liquefaction. A reaction time, i.e. a time where the temperature is held at the intended minimum during liquefaction, of below one minute is preferred according to the present invention.

As mentioned above, preferably the liquefaction is performed at a sub-critical condition for the HCW, which implies a temperature of below 374° C.

The process according to the present invention is preferably performed in a continuous flow system, such as in a tube, possibly intended for pre-treatment and liquefaction. However, also separate units may be used, depending on the aim of the liquefaction. For example, according to one specific embodiment of the present invention, the liquefaction is performed sequentially in at least two "separate" reactors, and wherein separation of a liquid phase is performed after each reactor. This may be performed by e.g. feeding a biomass slurry into a continuous first flow reactor in which part of the biomass is liquefied, such as e.g. the hemicelluloses, then separating a first liquid phase solution, thereafter feeding the biomass slurry containing the solid material into a continuous second flow reactor in which at least part of the remaining biomass is liquefied, and then separating a second liquid phase solution, and hence water and water soluble components, from the optionally remaining biomass slurry being discharged from said second flow reactor. Moreover, although the flow reactors are mentioned as separate reactors, they may also be different parts of one and the same tube reactor having different portions for different liquefactions and separations and so forth. As understood from above, the method according to the present invention may also comprise removal of non-solubilised material, and also comprise the reprocessing of such removed non-solubilised material.

According to one embodiment a first liquefaction is preferably performed to bring forth the hemicellulose of the biomass and degrade that into monomers and oligomers. The temperature of a first liquefaction is preferably between 200 and 280° C. For example the lower temperature of the range may be 220, 230, 240 or 250° C. Preferably the temperature is in the range 240-260° C. or 250-280° C. The reaction time for the liquefaction is below 1 minute, e.g. in the range 1 to 45 seconds, 1.5 to 30 seconds, or 1.5 to 15 seconds. The conditions of the thermal treatment are here within the subcritical range. However, hot compressed liquid water (HCW) at subcritical and/or supercritical conditions may be injected into the reactor containing the biomass. If HCW at supercritical condition is injected in to the reactor, the degradation of the biomass takes place at subcritical conditions due to a decrease in temperature when brought into the reactor.

After a first liquefaction the water soluble and liquid materials may be separated from the remaining solids. Such a separation may be performed by decantation, centrifugation and/or filtration. A separation step may be performed at a temperature of 20-280° C., e.g. at 80-200° C., such as around 100° C.

The remaining solids after the first liquefaction may then be subjected to a further liquefaction. Such a second liquefaction is then performed at a higher temperature to convert the remaining cellulose of the used biomass into monomers and oligomers. By subjecting the remaining solids to hot compressed liquid water (HCW) at subcritical or supercritical conditions monomers and oligomers are obtained from the degradation of cellulose. The reaction time for the second liquefaction is also below 1 minute, e.g. in the range 1 to 45 seconds, 1.5 to 30 seconds, or 1.5 to 15 seconds. As stated previously the pH for this second liquefaction is within the ranges disclosed above, i.e. at most 4, preferably with in a range of 1-4, such as 1.2-3.3, 2.0-3.1, 2.3-3.1, 2.5-3.0, 2.5-2.8, 2.55-2.75, or 2.60-2.75.

If more than one liquefaction is performed sequentially the pH need not be the same in all the sequential thermal treatment steps. The pH may vary from liquefaction to liquefaction.

After this second liquefaction, if there are any remaining solid materials, the water soluble and liquid materials are separated from the remaining solids. Such a separation may be performed by decantation, centrifugation and/or filtration. According to one specific embodiment of the present invention, the liquefaction is performed in hot compressed liquid water (HCW) at a sub- and/or super-critical condition. It should be said that the liquefaction may also be performed in mixtures at a sub- and/or super-critical condition, for instance in a mixture of HCW together with amounts of acids, carbon dioxide or ethanol. Bases may be used to slow down or quench the liquefaction. To use HCW, possibly with addition of some acid(s), is however preferred as the solvent for the liquefaction according to the present invention.

As hinted above, the process according to the present invention is preferably performed in a continuous flow system, such as a tube, however the principle may also be used for batch or semi-batch systems. Also processes in such systems are embodied by the present invention.

EXAMPLES

Figure 1:
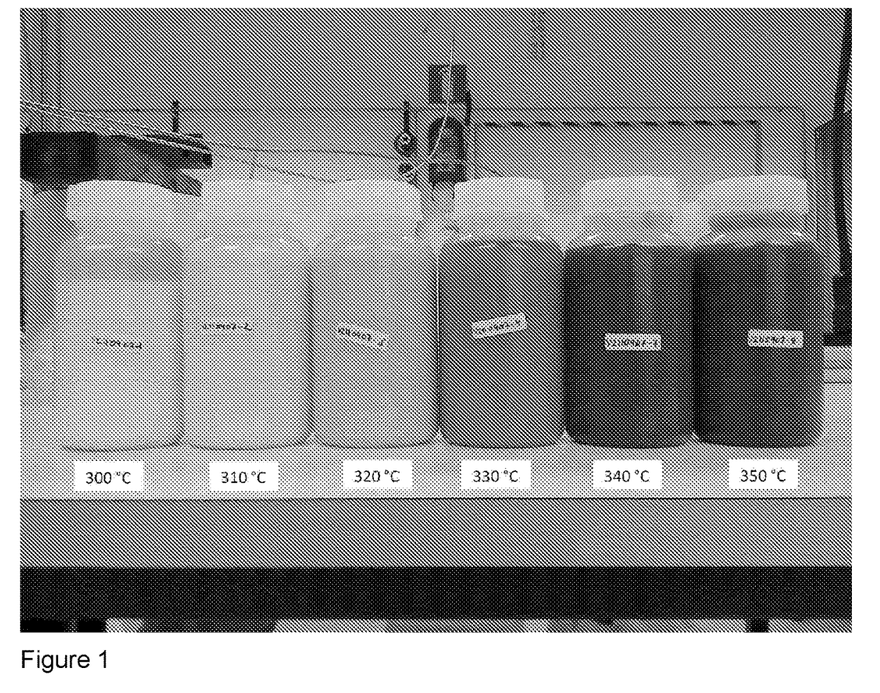
FIG. 1 shows six samples taken from the experiment of Examples, where 10 wt % cellulose, and a residence time of 1.6 seconds was used.
Figure 2:
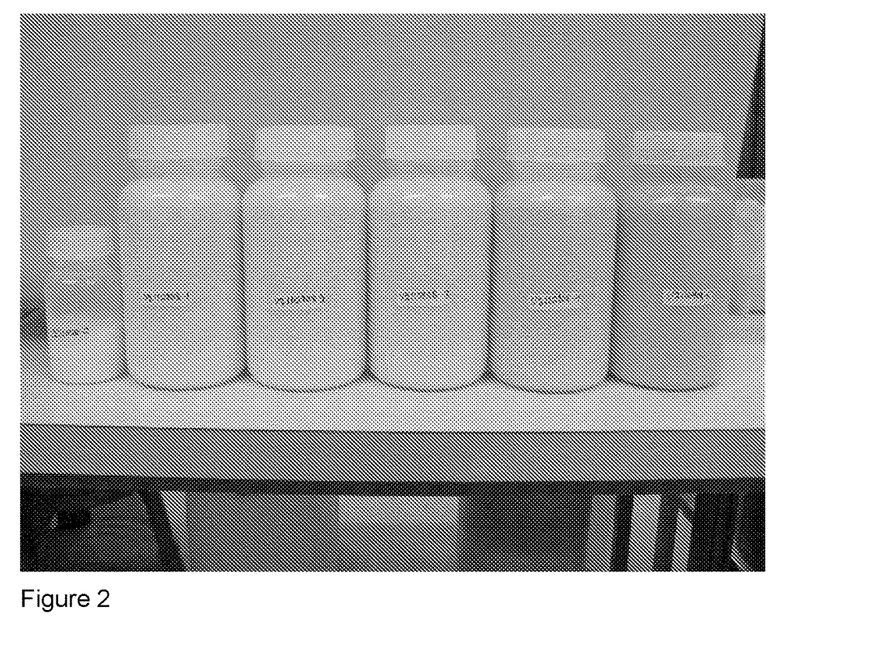
FIG. 2 shows five samples (the large bottles) taken from the experiment of Examples where, 10 wt % cellulose, a residence time of 1.6 seconds and an increased pH obtained by adjustment by NaOH was used. The bottles show the results of increasing temperature from left to right (300, 310, 320, 330, and 340° C.). The small bottle to the far left contains unprocessed cellulose slurry.

Tests were performed on cellulose. A cellulose feedstock containing 10 wt % cellulose and the remainder being water was feed into a reactor. The cellulose containing samples were in turn subjected to liquefaction by injection of hot compressed liquid water. The reaction temperature for the cellulose containing samples were varied (300, 310, 320, 330, 340 and 350° C.) for the different samples but the residence time at the reaction temperature was kept the same, 1.6 seconds for all samples. From table 1 it is clear that an increase in temperature and a decrease of the pH results in a higher amount of degraded material shown as the obtained monomer yield. The next series of tests were performed in the same way except for that the pH was amended, i.e. increased for the tests by using NaOH. From table 2 it is clear that a higher pH influences the degradation process negatively even at higher temperatures. The results of table 1 and 2 clearly show that a slight amendment of the pH has a large impact on the degradation of the cellulose material. Also, when looking at the FIGS. 1 and 2 the visual appearance is different between the tests. From FIG. 1 it is clear that the colour change of the samples processed at higher temperatures are influenced differently by the liquefaction.

TABLE 1

10% Cellulose without pH adjustment (1.6 s residence time):

| Temperature (° C.) | pH | Monomer yield in % (including erythrose and anhydroglucose) | Remaining water insoluble cellulose (%) |
| --- | --- | --- | --- |
| 300 | 3.74 | 2.7 | 82.3 |
| 310 | 3.45 | 3.5 | 77.2 |
| 320 | 3.16 | 9.8 | 48.8 |
| 330 | 2.96 | 30.6 | 11.0 |
| 340 | 2.73 | 65.8 | 0.2 |
| 350 | 2.6 | 73.3 | 0.3 |

TABLE 2

10% Cellulose with pH adjustment by NaOH (1.6 s residence time):

| Temperature (° C.) | pH | Monomer yield in % (including erythrose and anhydroglucose) | Remaining water insoluble cellulose (%) |
| --- | --- | --- | --- |
| 300 | 3.96 | 0.3 | 90.5 |
| 310 | 3.8 | 0.4 | 92.7 |
| 320 | 3.67 | 0.5 | 89.6 |
| 330 | 3.41 | 1.0 | 82.5 |
| 340 | 3.21 | 1.7 | 70.0 |

More Aspects of the Present Invention

Below, more aspects of the present invention are disclosed. This aspect is related to the quenching of the biomass liquefaction.

A Second Aspect of the Present Invention

According to a second aspect of the present invention there is also disclosed a method for quenching a liquefaction reaction of a lignocellulosic biomass starting material, to avoid continued detrimental decomposition, for the production of a monomer and/or oligomer sugar mixture solution. The quenching according to the present invention may be performed so that lignin is solidified very rapidly and may as such be separated and collected.

It has long been known to quench different types of reactions. Quenching implies stopping the reaction or slowing it down and this may be performed by different means, such as by lowering the temperature, reducing the pressure, adding substances, etc. Moreover, to quench different forms of biomass reactions has also been described. For example, in WO 01/88258 there is disclosed a continuous process for the conversion of biomass to form a chemical feedstock. The biomass and an exogenous metal oxide, preferably calcium oxide, or metal oxide precursor are continuously fed into a reaction chamber that is operated at a temperature of at least 1400° C. to form reaction products including metal carbide. The reaction products are quenched to a temperature of 800° C. or less. The resulting metal carbide is separated from the reaction products or, alternatively, when quenched with water, hydrolyzed to provide a recoverable hydrocarbon gas feedstock.

Furthermore, in WO2007/128798 there is disclosed a process for converting a solid or highly viscous carbon-based energy carrier material to liquid and gaseous reaction products, said process comprising the steps of: a) contacting the carbon-based energy carrier material with a particulate catalyst material b) converting the carbon-based energy carrier material at a reaction temperature between 200° C. and 450° C., preferably between 250° C. and 350° C., thereby forming reaction products in the vapor phase. The process may comprise the additional step of: c) separating the vapor phase reaction products from the particulate catalyst material within 10 seconds after said reaction products are formed; and d) quenching the reaction products to a temperature below 200° C.

Moreover, to quench e.g. the liquefaction of biomass, for instance being performed in sub- or super-critical conditions, has also been addressed in the past. For instance, in US2010/0063271 A1, there is disclosed a "dynamic" supercritical fluid biomass conversion system for continuously converting a selected biomass material into a plurality of reaction products, and comprises, in fluidic series: a biomass conveying zone; a supercritical fluid biomass conversion zone within an electrically conductive housing and about a central axis; and a reaction product quenching/separation zone. According to the examples, it is disclosed that the fully loaded pressure vessel was subjected to a time-variable magnetic field by energizing the induction coil with alternating electric current that ranged from about 50-100 KHZ for a period of time ranging from about 2 to 5 seconds. After energizing, the vessel was rapidly cooled by way of quenching with a cascading flow-stream of water.

The present invention is as such also directed to providing an optimal method for quenching a biomass material which has undergone liquefaction in a sub- or super-critical condition.

Summary of a Second Aspect of the Invention

The stated purpose above is achieved by a method for quenching a liquefaction reaction of a lignocellulosic biomass starting material, said liquefaction reaction being performed at a sub- and/or super-critical condition for the production of a monomer and/or oligomer sugar mixture solution, wherein the quenching is made to avoid continued detrimental decomposition, and wherein the quenching is performed by injection of water into the monomer and/or oligomer sugar mixture solution, for a rapid cooling of the solution so that liquid lignin components or liquid lignin derivative components are solidified instantly. The rapid solidification of the lignin according to the present invention has several advantages, such as the avoidance of fouling and clogging problems of sticky lignin adhering to inner surfaces of process equipment, like tubing, and as such the provision of a lignin phase which is comparatively easy to separate and collect. The solid lignin phase that is possible to create according to the present invention may be separated from a solution holding other fractions, both solid and liquid. Such solid components may be e.g. undissolved cellulose and other possible particles. The liquid fraction consists mainly of the monomer and/or oligomer sugar mixture solution. It should, however, be noted that it is desirable to prevent to separate the solid lignin phase from solid cellulose, and therefore it is better to separate and remove such cellulose before injecting cold water, and thus before solidifying the lignin components, according to the present invention.

The expression "rapid cooling" should be interpreted as imply at least a cooling needed to solidify liquid lignin components or liquid lignin derivatives before a substantial amount of these become sticky and may adhere to process equipment (see below). As may be understood, to be able to cool rapidly, several parameters have importance, such as the temperature of the monomer and/or oligomer sugar mixture solution when this is about to be quenched, the flow and/or volume of this mixture solution, the flow of the injected quenching water and of course also the temperature of the injected quenching water. Different embodiments of the present invention in relation to this matter are discussed below.

In relation to the solidification of the lignin components or liquid lignin derivative components, which are in liquid state after the liquefaction, it should be said that the solid state of this components may be in different forms and shapes, such as crystals, e.g. spikes, "icicles", particles, clumps, clusters, or the like. Nevertheless, the purpose according to this aspect of the present invention is to transform the lignin components to a solid state very rapidly so that they do not become sticky and as such may clog process equipment, such as tubing, piping, subsequent heat exchanges or the actual liquefaction reactor(s). The cold water injection according to the present invention ruptures the lignin components in the dispersion and rapidly cools these components to a solid state. Moreover, the cold water injection also quenches the degradation of monomers.

During normal cooling of liquid lignin components they are transformed from a liquid state to a solid state, however, when they pass their sticky state they are very difficult to handle during processing. Firstly, in a sticky state they are difficult to extract from a process, and as such a possible high fraction of these components are lost in yield. As lignin components may be of high-value, this is undesirable. Secondly, when they go lost, they have often adhered to surfaces of the process equipment, and as such they contribute to fouling and/or clogging problems in the equipment. Furthermore, one important aspect of the problem discussed above is the fact that the temperature range wherein the lignin is sticky and gluey is comparatively wide, about 10 to about 20° C. or more in width. This is one of the important aspects why the rapid cooling ensuring an instant solidification of lignin according to the present invention is so advantageous.

To extract lignin components after liquefaction processes of biomasses in a sub- or super-critical condition has been addressed in the past. For instance, in US2010/0043782 there is disclosed a process for producing xylose and cellulose from a biomass comprising mixing a biomass with a reactive fluid comprising water and a supercritical $C_1$-$C_5$ alcohol to form a mixture at a first temperature and a first pressure, maintaining the mixture at the first temperature and first pressure for a first time period, wherein a reaction occurs, and quenching the reaction to form at least one reaction product mixture, wherein xylose and cellulose are produced by the process. Lignin is also said to optionally be produced by the process. In the process, the reaction at the single stage fractionation of biomass or at each stage of the two stage fractionation process may be quenched by addition of cooled solvent, for example, cooled water/$C_1$-$C_5$ alcohol. The process is said to be directed to avoiding lignin precipitation via the addition of alcohol to the water phase, which allows both cleanly fractionated cellulose and high quality lignin to be separately recovered. Via the addition of the alcohol, the lignin is dissolved and leaves cellulose in the solid phase, and the two substances are separated by filtration. Lignin is precipitated after evaporation of the added alcohol, and may be collected after filtration.

As understood from above, the process according to the present invention, handles the lignin components very differently in comparison to the process of US2010/0043782. According to the present invention, the lignin components are solidified during the quenching by injection of water, and not by adding a lignin solvent, such as an alcohol. Moreover, as such lignin may be separated directly after the quenching according to the present invention without the need for any subsequent steps, such as the evaporation of alcohol according to US2010/0043782.

Another process is described in WO2011/091044, discussed above, which discloses methods for the continuous treatment of biomass, comprising a pre-treatment step, wherein said biomass is contacted with a first supercritical, near-critical, or sub-critical fluid to form a solid matrix and a first liquid fraction; and a hydrolysis step, wherein said solid matrix formed in said pre-treatment step is contacted with a second super-critical or near-supercritical fluid to produce a second liquid fraction and an insoluble lignin-containing fraction. According to the processes disclosed in WO2011/091044, water, possibly containing acid, may be introduced into the reactor for quenching. According to the process disclosed in WO2011/091044, it is intended to keep the lignin in an insoluble state so that a liquid fraction containing xylose and a solid fraction containing cellulose and lignin may be separated after pre-treatment, such as via skimming or filtration. It is also mentioned that the temperature of the hydrolyzed slurry may be reduced such that the lignin precipitates, possibly without the addition of a precipitation or flocculating agent.

Also WO2011/091044 is related to a different process than the present invention. Firstly, the process according to WO2011/091044 aims at keeping the lignin in an insoluble state. The process according to the present invention, however, is related to instant solidification of liquid, i.e. solubilised, lignin or derivates thereof. Secondly, the precipitation of that possible fraction having solubilised lignin, which is suggested in WO2011/091044, is related to a temperature reduction in general, possibly without the addition of a precipitation or flocculating agent. According to the present invention, however, a rapid cooling involving the injection of cold water is involved, said rapid cooling performed for instant solidification of lignin components or derivates thereof. The process according to the present invention handles and extracts the lignin components by a very different route than the one disclosed in WO2011/091044. As such, the present invention also provides a solution to the fouling and clogging problems with lignin when this is transformed from a liquid to a solid state. WO2011/091044 is not related to this problem and, hence, does not provide a solution to this problem.

Specific Embodiments of the Invention

Below specific embodiments relating to this aspect of the present invention are disclosed. First of all it should be mentioned that although the present invention, according to this aspect, is directed to quenching the liquefaction of a lignocellulosic biomass, different types of biomass starting materials may be possible to use according to the present invention. Both hardwood and softwood biomass types are possible, and the lignin content varies in such different types. Furthermore, the lignin content may also vary within one specific type of biomass.

As disclosed above, the process according to the present invention may be seen as a process involving at least two steps, one liquefaction step and one quenching step. Pre-treatment before the liquefaction as well as separation steps may also be included in the process. Nevertheless, the preceding liquefaction is an important step of the present invention. According to one specific embodiment of the present invention, the liquefaction is performed in hot compressed liquid water (HCW) at a sub- and/or super-critical condition. It should be said that the liquefaction may also be performed in mixtures at a sub- and/or super-critical condition, for instance in a mixture of HCW together with amounts of acids, carbon dioxide or ethanol. To use HCW, possibly with addition of some acid(s), is however preferred as the solvent for the liquefaction according to the present invention.

As notable from above, the liquefaction may be performed in "sub- and/or super-critical condition" which implies that both of these conditions are possible as well as a combination where one first liquefaction step first may be performed in e.g. a sub-critical condition and a second liquefaction step mat be performed in e.g. a super-critical condition. The quenching according to the present invention may as such also be performed after a first such liquefaction step, where after lignin components may be separated, which in turn implies that a second quenching, after a second liquefaction, may be performed without the solidification of lignin components if no such are present. In relation to the above stated it should be mentioned that the liquefaction according to the present invention preferably is performed in a sub-critical condition for HCW, but above 200° C. Therefore, according to one specific embodiment of the present invention, the liquefaction is performed in a temperature of at least 200° C. A biomass comprises cellulose, hemicelluloses and possibly lignin. As hemicelluloses dissolve at a lower temperature than cellulose, however at a higher temperature than lignin, the temperature for the liquefaction may vary and depends on the intended liquefaction. According to the present invention, it may be of interest to separate the lignin phase at the same time as hemicelluloses are separated, that is before cellulose is liquefied in a subsequent step. Therefore, according to one specific embodiment of the present invention, the liquefaction is performed at a temperature in the range of 200-300° C., such as 220-280° C. or 225-265° C. Thereafter, the cold water injection is performed to solidify and remove the lignin phase, before e.g. another liquefaction of a cellulose phase. For dissolving hemicellulose effectively, the temperature should preferably be held at least 230° C., preferably at least 250° C. As such these temperatures may be seen as preferred minimum levels for the liquefaction according to the present invention.

For dissolving cellulose, the temperature should be at least 280° C. According to the present invention, lignin may instead be separated after such a liquefaction, for instance if that is the sole liquefaction step. Therefore, according to one specific embodiment of the present invention the liquefaction is performed in a temperature of at least 280° C. Also the reaction time is an important parameter. According to the present invention, the reaction time should be held short, irrespective if e.g. a semi-batch or a continuous flow system is used for the liquefaction and quenching. A reaction time, i.e. a time where the temperature is held at the intended minimum during liquefaction, of from below 1 s up to 30 s, such as from 1.5 to 30 s, is a preferred range according to the present invention. It should be noted that also the feeding of the biomass feedstock as well as the loading of HCW, may be performed differently, and by different mixing alternatives.

As said above, preferably the liquefaction is performed at a sub-critical condition for the HCW, which implies a temperature of below 374° C. A preferred range for the liquefaction, when aiming for the cellulose liquefaction, is a temperature range of 280-350° C., e.g. 300-350° C. According to this aspect of the present invention it should be said that if the liquefaction is performed without the addition of a pH lowering additive (acids) according to the present invention, the temperatures needed will be comparatively higher. An example is a first hemicellulose dissolution step where the temperature is in the range of 200-270° C., normally not much lower than 250° C., and a second cellulose dissolution step where the temperature is held above 300° C. Such a process is also embodied according to the present invention.

The process according to the present invention is preferably performed in a continuous flow system, such as in a tube, possibly intended for all of pre-treatment, liquefaction and quenching. However, also separate units may be used, depending on the aim of the liquefaction. For example, according to one specific embodiment of the present invention, the liquefaction is performed iteratively in at least two "separate" reactors, and wherein separation of a liquid phase is performed after each reactor. This may be performed by e.g. feeding a biomass slurry into a continuous first flow reactor in which part of the biomass is liquefied, such as e.g. the hemicelluloses, then separating a first liquid phase solution, and hence water and water soluble components, performing a quenching of this first liquid phase solution for the solidification and then separation and recovery of lignin, then feeding the biomass slurry containing the solid material into a continuous second flow reactor in which part of the remaining biomass is liquefied, and finally separating a second liquid phase solution, and hence water and water soluble components, from the biomass slurry being discharged from said second flow reactor. Depending on the intended temperatures used in the different flow reactors, the optimal point where the quenching is to take place for solidification of the lignin components may vary. Moreover, although the flow reactors are mentioned as separate reactors, they may also be different parts of one and the same tube reactor having different portions for different liquefactions and separations and so forth. As understood from above, the method according to the present invention may also comprise removal of non-solubilised material, and also comprise the reprocessing of such removed non-solubilised material.

The post-quenching temperature of the monomer and/or oligomer sugar mixture solution is of importance for the present invention. Post-quenching temperature is the temperature of the entire mixture after cold water has been injected. Lignin does not have a specific melting point, but may be said to have a melting point range, normally between about 170-180° C., depending on the biomass type, the contained lignin therein, the particles size, the processing thereof and the degradation level of it. As lignin should be rapidly solidified, it is important to reach a temperature below the above mentioned range very rapidly. In relation to this, it should also be said that the injection of cold water should be performed to ensure the disruption of the liquid lignin phase into small fragments, which in turn accelerates the cooling. According to one specific embodiment, the quenching is performed by injection of water into the monomer and/or oligomer sugar mixture solution to a post-quenching temperature below 165° C., preferably below 150° C. It is of course possible to use a lower post-quenching temperature, but this depends on several parameters, and is also a question of optimization and energy consumption. For example, if a large flow of cold water is injected, the intended post-quenching temperature is possible to reach quicker. Both temperature and time is of importance for the quenching. For instance, it is not interesting to slowly cool the lignin, which as such will pass its sticky phase and hence adhere to the process equipment. Instead the cooling should be made very rapidly and to a temperature well below the melting point range of lignin. Therefore, according to one preferred embodiment of the present invention, the quenching is performed so that the post-quenching temperature is reached within a time of maximum 10 seconds. The needed time also depends on several parameters, such as type and size of system used, e.g. tubing diameter, etc. According to one specific embodiment of the present invention, the post-quenching temperature is reached within a time of maximum 2 seconds, e.g. within a time of maximum 1 second. Quenching times of below 1 second, or at least below 2 seconds, are preferred, and should be seen as suitable set points value for continuous flow systems like tubes.

It should be said that quenching may be performed differently according to the present invention. According to one specific embodiment, the quenching step is performed by flash cooling. Flash cooling is normally performed in several steps according to the present invention. As an example, the first flash or quench may be performed to a temperature of e.g. below 220° C., such as below 215° C. but above 200° C., while a second flash may be made to a temperature of around 150° C., such as in the range of 130-170° C. This second flash may transform dissolved lignin to solid quickly without risking clogging or fouling. This solid lignin may then be removed by a separation technique.

It should clearly be stated that the flashing may be performed in just one step also, such as directly to a temperature of e.g. 150° C., according to the present invention to achieve an effective quenching step allowing for subsequent lignin removal. However, from an energy efficiency point of view several steps may be beneficial.

As hinted above, the process according to the present invention is preferably performed in a continuous flow system, such as a tube, however the principle may also be used for batch or semi-batch systems. Also processes in such systems are embodied by the present invention.

Furthermore, although the size and shape of the solidified lignin may vary depending on the exact process parameters, the used biomass type, etc., they may be called microparticles. As is also mentioned, these solidified lignin components are preferably separated and collected, as they are of high-value. The separation may be performed in different ways, e.g. by use of filtration or centrifugation. Possible devices to use are e.g. centrifuges, hydrocyclones, or filters, such as continuous self-cleaning filters or batch filters. A preferred choice may be to separate by filtration as this is a lenient technology to use for the lignin solids, which may be of relevance.

EXAMPLES

Trials have been performed in a continuous flow system, namely a tube reactor. One of these experiments was conducted according to the following. A biomass starting material, based on spruce with a 2% dry matter level, was used. A liquefaction of the biomass feedstock was performed in HCW and the reaction temperature was set to 325° C. in a reactor tube. The effect of the injection of cold water was investigated. Cold water was injected into the product flow after that said product flow had passed a cooler positioned after the reactor. The temperatures set were about 200° C. for the product flow out from the cooler and 120° C. in the mixing point, i.e. for the mixture after cold water had been injected. Then, this mixture was fed to a capillary with a total length of 16 m (2 capillaries, each 8 m, in series).

It should be mentioned that trials have also been performed where the cooler after the reactor has been excluded and where the injection of cold water is the sole cooler of the flow stream.

The trials were conducted according to the following. Firstly, water is pumped through the system, to obtain the right temperatures. Then the feeding is switched to biomass feeding (slurry) into the process system. The cold water injection is run in operation during the entire phase. The differences between just running water feed through the system and the slurry feed was investigated, and the influence on providing the cold water injection. The effects of feeding water and slurry, respectively, were investigated by looking at the pressure drop across the capillary. The pressure drop across the capillary was constant over a certain time when switching from water to slurry. Although there was an increased pressure drop observed when feeding slurry, there were positive results in comparison to other trials without cold water injection. In other words, the injection of water delayed the clogging of the capillary, which in turn was caused by the water injection having a dispersive effect on the lignin.

A Third Aspect of the Present Invention

According to a third aspect of the present invention there is also provided a method for preventing, minimizing or eliminating clogging and/or fouling of biomass components in process equipment, such as during the processing of a liquefaction of biomass as according to above.

The problems of fouling exist in many different kinds of processes and are well known. As is described on e.g. Wikipedia, fouling may be described as the accumulation of unwanted material on solid surfaces, such as surfaces in reactors, tubing/piping or for instance in heat exchangers, or the like. Fouling may also be called deposit formation, deposition, scaling, slagging, and sludge formation, but also other terms are used. Furthermore, fouling may be divided into different categories, such as precipitation fouling, e.g. crystallization, particulate fouling, i.e. the accumulation of particles on a surface, corrosion fouling, chemical reaction fouling, and e.g. solidification fouling, the latter happening when components of a flowing fluid with a high-melting point freeze onto a sub-cooled surface.

As is known, fouling causes many problems, e.g. impaired heat transfer, corrosion damage, increased pressure drop, and flowing problems, such as flow blockages, etc. The most used method of controlling fouling today is the prevention of ingress of the fouling species into the cooling water circuit. In the case of micro fouling, water purification may be achieved with extensive methods of water treatment, filtration and e.g. membrane technology. The generation of corrosion products in water tubing systems is inter alia minimized by controlling the pH of the process fluid (typically by alkalization with ammonia, morpholine, or ethanolamine), e.g. in the paper pulp industry. For instance in U.S. Pat. No. 3,413,189, there is disclosed the hydrolysis and subsequent digestion of cellulosic fiber material in a vessel through which the material is continuously advanced with the separation from the fiber material and discharge together of hydrolysate and spent liquor, where a portion of the digesting liquor is introduced in the vicinity of the hydrolysate and spent liquor mixing, whereby precipitation of alkali lignin out of the spent liquor is minimized or prevented, such as by raising the pH value up to approximately 10-11.

Other methods used for the minimization of corrosion products or that kind of fouling are to control of oxygen dissolved in water (e.g. by addition of hydrazine), or addition of corrosion inhibitors. Moreover, chemical fouling inhibitors may reduce the fouling in many systems. Examples of such are e.g. chelating agents, different types of amines, and e.g. polyacrylic acids.

Moreover, it is known that there also may exist fouling problems in biomass processes. For instance, in US2005/0039599 there is disclosed the continuous collection of aerosol and liquid droplets from the gas stream resulting from a pyrolysis/thermolysis of biomass process before it causes fouling and coking/carmelization and, therefore, operation stoppage of downstream equipment. The method involves the capturing of BioOil, i.e. the liquids produced from biomass using the fast pyrolysis process, and its constituents from a gas stream produced in a fast pyrolysis/thermolysis process, and the separating of BioOil and its constituents from a gas stream using hot inertial separation to maintain the temperature of said BioOil and its constituents above a temperature at which the thick and/or sticky constituents cause inefficient operation of the equipment but low enough so that they do not undergo rapid degradation.

Furthermore, in US2002/0148575 there is disclosed a multi-function process described for the separation of cellulose fibers from the other constituents of lignocellulosic biomass such as found in trees, grasses, agricultural waste, and waste paper with application in the preparation of feedstocks for use in the manufacture of paper, plastics, ethanol, and other chemicals. The process is said to minimize waste disposal problems since it uses only steam, water, and oxygen at elevated temperature in the range of 180-240° C. for 1 to 10 minutes plus a small amount of chemical reagents to maintain pH in the range 8 to 13. The process involves subjecting the feedstock to a counter-flow of hot wash water containing dissolved oxygen and having a pH of at least 11 to produce residual solids containing cellulose and a wash water containing lignin and other extractives, where the residual solids containing the cellulose are separated.

One purpose of the present invention is to provide a method for preventing, minimizing or eliminating fouling problems during the processing of biomass. Another purpose of the present invention is to provide a method which is optimal for preventing, minimizing or eliminating fouling problems during a liquid processing of a biomass, especially during or after the processing of a biomass in a liquid solution at temperatures above 200° C., at least above 150° C.

Summary of a Third Aspect of the Invention

The stated purpose above is achieved by a method for preventing, minimizing or eliminating clogging and/or fouling of sticky biomass components in process equipment, wherein an alkaline liquid is washed through the process equipment, either as a sole solution between regular process operations of a biomass process flow in a liquid solution, or as added directly into the liquid solution for dissolving biomass components which are or otherwise may become sticky.

In relation to this aspect of the present invention, process equipment may be seen as everything that may come in contact with the biomass solution, such as tubing or piping, a reactor, such as a batch or a continuous tube reactor, but also other units, such as e.g. pre-heaters or heat exchangers, or the like. Moreover, the term "biomass components" should be interpreted as any possible component contained in the solution, implying both components being in the same form as before the processing as well as components which have a different form during or after the processing, or in fact new components which have been produced during the processing. As noted, the main components of interest to take care of according to the present method are the ones that may become sticky during the processing and therefore have high risk of adhering to the process equipment, i.e. the ones which cause fouling. One example of such components is lignin or lignin derivates, which may cause a large fouling problem. Lignin may be liberated from the biomass at perhaps from 80 to 100° C. Lignin does not have a specific melting point, but may be said to have a melting point range, normally between about 170-180° C., depending on the biomass type and contained lignin. Above such temperatures in water, part of the lignin may be dissolved in the liquid, however functioning in a two-phase system as a hydrophobic component, i.e. droplets or an emulsion component. If the lignin is cooled again below the temperature range, it solidifies and may as such cause severe fouling problems. Lignin passes a sticky phase when being cooled, and as such it may adhere to inner surfaces of the process equipment. Once being cooled down to much lower temperatures, the lignin has already adhered to these surfaces and is then very difficult or impossible to remove from the equipment if not being forced such as according to the present invention. Furthermore, one important aspect of the problem discussed above is the fact that the temperature range wherein the lignin is sticky and gluey is comparatively wide, about 10 to about 20° C. in width. The so called solidification fouling occurs when a component of a flowing fluid "freezes" onto a surface forming a solid fouling deposit. As may be understood from above, when heating a solution containing lignin components, or the like, passing the sticky phase from that way may of course also cause fouling or clogging problems. Both processing directions, that is when lignin has been heated or cooled slowly enough to become sticky and then cause fouling or clogging problems, are situations which are addressed by the present invention.

In a more alkaline environment, the solubility of lignin increases. This may be one of the driving forces for the method according to the third aspect of the present invention.

It should be said that there are also other components besides lignin, such as e.g. some degradation products depending on the biomass starting material that may be of interest to take care of according to the present invention.

As stated above, the present invention is related to liquid solutions comprising biomass, both possible solid components of the biomass as well as components which have been liquefied. Taking care of wood processing, processes during pulping, or the like, before having an actual biomass are not considered. Such processing may, however, be seen as possible pre-treatments before the method according to the present invention.

As understood from above, one important aspect of the present invention is related to lignocellulosic biomasses, implying that the biomass components which are or otherwise may become sticky are lignin components or lignin derivative components. There may also be other such components, but lignin is of course the main component.

According to one certain embodiment of the present invention, the alkaline liquid is added into the biomass process flow solution either into a reactor or after said reactor for quenching of a decomposition of the biomass starting material. As such, the alkaline liquid is both used for taking care of the fouling and clogging problems, but also to aid in stopping the reaction. In relation to this aspect of the present invention, it should be clearly understood that also washing a system between processing sequences, i.e. when the alkaline liquid never is brought into contact with the biomass solution but only used as a flushing liquid, or as used only before an actual decomposition reaction, that is not for quenching reasons, are also processes embodied by the present invention. One other possibility is for example to combine the use of alkaline solution according to the present method and another type of quenching method. One such example is combine the use of alkaline solution before the decomposition according to the present invention, and then use cold water injection for quenching the actual decomposition reaction. This is further explained below.

According to one specific embodiment of the present invention, the alkaline liquid is added into the biomass process flow solution either into a reactor or after said reactor for quenching a liquefaction reaction of the biomass starting material, said liquefaction reaction being performed at a sub- and/or super-critical condition for the production of a monomer and/or oligomer sugar mixture solution, wherein the quenching is made to avoid continued detrimental decomposition, and for said dissolution of the biomass components which are or otherwise may become sticky. Also additives may be present, such as e.g. acids or the like. Moreover, there may also be other solvents mixed into the HCW, such as carbon dioxide or ethanol, however using HCW as the sole solvent is preferred.

Problems of clogging during the use of sub- or supercritical fluid(s) and organic substances have been discussed before. For instance, in US2004/0094144 there is disclosed a reaction apparatus for organic and/or other substance(s) employing supercritical fluid(s) and/or subcritical fluid(s) permitting injection of organic substance(s) and/or other reactant substance(s) in homogeneous state(s) to reactor(s) without occurrence of clogging at location(s) of such injection, and also permitting actuation to occur in industrial fashion and at high energy efficiency. Because fine wood meal can be dispersed in this spray due to the fact that cold water can be sprayed at high velocity, and because wood meal can be propelled with saturated liquid, it is possible to prevent occurrence of clogging of spray nozzle(s). The apparatus and process is, however, not related to washing or quenching with an alkaline liquid. The only possible use of e.g. alkali disclosed in US2004/0094144 is related to the decomposition of the possible reactants PCB, R-series refrigerant, DXN, dioxin and/or other such decomposition-resistant halogen-containing substances.

Furthermore, in JP2008142599A there is also disclosed a method for preventing clogging caused by fluidized elements from biomass, where alumina particles are used in a supercritical water gasification system.

Moreover, in US2008/0029233 there is disclosed a moving bed biomass fractionation system involving counter-current extraction of lignocellulosic biomass. The method disclosed in US2008/0029233 is said to include the continuous counter-current flow of biomass and reactive liquids, and the control of degradation reactions to increase product yields. The method includes feeding the biomass feedstock into a first stage of a pressurized reaction vessel, injecting a first wash liquid into the first stage counter-currently to the biomass feedstock, discharging the first wash liquid from the first stage, and discharging a solid biomass product from the reaction vessel in slurry form. The process may also include conveying a first stage biomass product from the first stage to a second stage of the reaction vessel, injecting a second wash liquid into the second stage counter-currently to the first stage biomass product, and discharging the second wash liquid from the second stage. The first wash liquid can include water or a solution of water and a mineral acid for hemicellulose hydrolysis, and the second wash liquid can include water and a sodium or ammonium hydroxide base for lignin hydrolysis. Furthermore, it is stated in US2008/0029233 that the means for discharging a processed biomass from the reaction vessel may include a processed biomass discharge progressive cavity pump configured to reduce pressure while avoiding clogging from settling solids.

The method disclosed in US2008/0029233 is not related to the use of an alkaline liquid for the prevention, minimization of elimination of clogging and/or fouling of biomass components. The possible second wash liquid which may include water and a sodium or ammonium hydroxide base is used according to US2008/0029233 as a reactant for driving lignin hydrolysis, and not as an anti-clogging or anti-fouling liquid. This is the fact both in terms of the possible use of the anti-clogging or anti-fouling liquid between processing steps as according to the present invention, and also when using this as a direct additive into the biomass liquid solution according to the present invention. Moreover, the second wash liquid according to US2008/0029233 is not used for quenching reasons, which may be the case according to one aspect of the present invention. Furthermore, the core concept of US2008/0029233 is to use counter-current processing, and US2008/0029233 is not related to prevention or elimination of fouling or clogging.

As mentioned above, the present invention finds specific use as a method involved in the process of liquefying a lignocellulosic biomass starting material in performed in hot compressed liquid water (HCW) at a sub- and/or super-critical condition.

As disclosed above, the process according to the present invention may be seen as a process involving at least two steps, one liquefaction step and one quenching step. Pre-treatment before the liquefaction as well as separation steps may also be included in the process.

As notable from above, the liquefaction may be performed in "sub- and/or super-critical condition" which implies that both of these conditions are possible as well as a combination where one first liquefaction step first may be performed in e.g. a sub-critical condition and a second liquefaction step may be performed in e.g. a super-critical condition. The quenching according to the present invention may as such also be performed after a first such liquefaction step, where after lignin components in liquid state may be separated in some way, and then collected, which in turn implies that a second quenching, after a second liquefaction, may be performed without the use of a alkaline liquid. Moreover, as hinted above, the actual quenching may be performed by different means than the use of alkaline solution, such as when the alkaline solution according to the present invention for instance is used between processing sequences or before the liquefaction. One quenching technology which is possible is by the use of injection of cold water for a rapid cooling so that liquid lignin components are solidified instantly into e.g. microparticles, which then may be separated and collected, before ever having had the possibility of adhering to inner surfaces and cause clogging problems.

In relation to the above stated it should be mentioned that the liquefaction according to the present invention preferably is performed in a sub-critical condition for HCW, but above 200° C. Therefore, according to one specific embodiment of the present invention, the liquefaction is performed in a temperature of at least 200° C. A biomass comprises cellulose, hemicelluloses and possibly lignin. As hemicelluloses dissolve at a lower temperature than cellulose, however at a higher temperature than lignin, the temperature for the liquefaction may vary and depends on the intended liquefaction. According to the present invention, it may be of interest to separate the lignin phase at the same time as hemicelluloses are separated, that is before cellulose is liquefied in a subsequent step. Therefore, according to one specific embodiment of the present invention, the liquefaction is performed at a temperature in the range of 200-300° C., such as 220-280° C. or 225-265° C. For dissolving hemicellulose effectively, the temperature should preferably be held at least 230° C., preferably at least 250° C. As such these temperatures may be seen as preferred minimum levels for the liquefaction according to the present invention.

For dissolving cellulose, the temperature should be at least 280° C. According to the present invention, lignin may be separated after such a liquefaction performed at a higher temperature than above, for instance if that is the sole liquefaction step. Therefore, according to one specific embodiment of the present invention the liquefaction is performed in a temperature of at least 280° C. Also the reaction time is an important parameter. According to the present invention, the reaction time should be held short, irrespective if e.g. a semi-batch or a continuous flow system is used for the liquefaction and quenching. A reaction time, i.e. a time where the temperature is held at the intended minimum during liquefaction, of from 1.5 to 30 s is a preferred range according to the present invention.

As said above, preferably the liquefaction is performed at a sub-critical condition for the HCW, which implies a temperature of below 374° C. A preferred range for the liquefaction, when aiming for the cellulose liquefaction, is a temperature range of 280-350° C., e.g. 300-350° C.

The process according to the present invention is preferably performed in a continuous flow system, such as in a tube, possibly intended for all of pre-treatment, liquefaction and quenching. However, also separate units may be used, depending on the aim of the liquefaction. For example, according to one specific embodiment of the present invention, the liquefaction is performed iteratively in at least two "separate" reactors, and wherein separation of a liquid phase is performed after each reactor. This may be performed by e.g. feeding a biomass slurry into a first continuous flow reactor in which part of the biomass is liquefied, such as e.g. the hemicelluloses, then separating a first liquid phase solution, and hence water and water soluble components, performing a quenching of this first liquid phase solution with an alkaline solution, which liquid phase containing at least most of the lignin may be separated, then feeding the biomass slurry containing the solid material into a second continuous flow reactor in which part of the remaining biomass is liquefied, and finally separating a second liquid phase solution, and hence water and water soluble components, from the biomass slurry being discharged from said second flow reactor. Depending on the intended temperatures used in the different flow reactors, the optimal point where the quenching by use of an alkaline solution is to take place may vary. Moreover, although the flow reactors are mentioned as separate reactors, they may also be different parts of one and the same tube reactor having different portions for different liquefactions and separations and so forth. As understood from above, the method according to the present invention may also comprise removal of non-solubilised material, and also comprise the reprocessing of such removed non-solubilised material.

As discussed above, the alkaline liquid may be used according to the present invention for quenching a liquefaction of a biomass. As the pH value of the liquefaction is a driver for the degradation of the cellulose and hemicelluloses into oligomers and monomers, increasing the pH value of the solution may function for stopping or at least slowing down a continued detrimental decomposition or degradation. During the liquefaction according to the present invention, the pH value of the solution should be below 4, preferably below 3.5, more preferred below 3. When high yields of wanted oligomers and monomers have been obtained and it is hence desirable to avoid a continued decomposition, the pH value may be increased to quench a continued degradation according to the present invention. According to the present invention, the alkaline liquid should preferably be added so that the pH value is increased above 5. Therefore, according to one specific embodiment of the present invention, the alkaline liquid is added to the biomass process flow solution for adjustment of the pH value of the biomass process flow solution from a pH value of maximum 4 before the adjustment and to a pH value of at least 5 after the adjustment. A range of the pH of 5.0-11.0 may be a suitable level for the pH after quenching.

As said above, the solubility of lignin also increases in a more alkaline environment. Therefore, it is possible according to the present invention to use the alkaline liquid after liquefaction for both quenching, however still keep at least a high fraction of the lignin components in a liquid state, although the temperatures of the solution is decreased and the lignin passes its sticky phase. After the quenching, it may of course be of interest to separate the fractions so that the monomer and/or oligomer sugar fraction as well as the lignin fraction may be extracted and collected. As such, according to one embodiment of the present invention, the alkaline liquid is processed separately from the biomass process flow solution after the washing or the addition thereof. In other words, also for the case when using the alkaline liquid for washing possible lignin fouling, such as by flushing sodium hydroxide pulses, between the liquefaction processings, if the lignin content is high, it is of interest to extract and collect.

In relation to the above it should be mentioned that the present invention also embodies a method where the alkaline liquid is used in the biomass solution before the actual liquefaction. In such case the lignin components are solubilised, separated and collected before the liquefaction.

Nevertheless, it is of interest to separate and collect lignin components or lignin derivative components according to the present invention, if such components exist in an amount worth mentioning. Such separation may be performed in different ways depending on where along the stream, i.e. upstream or downstream in relation to the liquefaction, the lignin phase should be separated and subsequently collected.

Furthermore, according to one specific embodiment, the alkaline liquid is recovered after the washing or addition thereof, for further washing or addition.

Different types of alkaline liquids may be used. According to one specific embodiment, the alkaline liquid is a liquid based on caustic liquor (sodium hydroxide/potassium hydroxide) or ammonia. A sodium hydroxide solution has been tested, which may be seen in the example description. As seen from the examples, also the concentration of the alkaline solution is of course of relevance. A concentration of about 3% for a sodium hydroxide (aq.) solution has been proven to be a suitable concentration level when being used for washing a liquefaction system as pulses flushed through the tubing. Higher concentrations are of course also possible, however this is related to the intended use, such as dependent on the alkaline solution being applied upstream or downstream. For example, when being used for quenching the liquefaction, different concentrations may be interesting to use for a quick quenching and increase of the pH value.

Also mixtures of different substances may be used in the alkaline liquid. Moreover, additives may be present. One such possible additive is one or several oxidizing agents which are added to increase the solubility of lignin or other components which may cause fouling or clogging problems. Examples are oxygen, air or e.g. hydrogen peroxide. One may say that these, if present, may function as an intensifier in the alkaline liquid. Another example of a possible additive is a dispersing agent. In relation to this it may be said that the dispersing agent(s) should preferably be dispersed throughout the material to which it is added. The dispersing of the dispersing agents may be done by mixing. The dispersing agents aid the liberation of the lignin from the structure it was previously locked in before or after the thermal treatment, making the lignin not as intertwined in the cellulose, as it used to be, and may assist in the formation of an emulsion or dispersion of the lignin in the formed sugar solution. Examples of dispersing agents are lignosulphonates, polyacrylates and SASMAC (a co-polymer of a sulphonated acrylate and maleic acid). Other examples are salts of lecithin, sulphonates and carboxylates. Preferred lignosulphonates are ammonium lignosulphonate, sodium lignosulphonate, calcium lignosulphonate, magnesium lignosulphonate, and ferrochrome lignosulphonate. Preferred polyacrylates are sodium, potassium, lithium and ammonium polyacrylates. Typical acrylate monomers used to form acrylate polymers are acrylic acid, methacrylate, acrylonitrile, methyl acrylate, ethyl acrylate, 2-chloroethyl vinyl ether, 2-ethylhexyl acrylate, hydroxy ethyl methacrylate, butyl acrylate, butyl methacrylate, and TMPTA. Also a dispersing agent may function as an intensifier in the alkaline liquid for dissolving the lignin or keeping the lignin dispersed.

It should further be said that the present invention also is directed to the use of an alkaline liquid as an additive to a lignocellulosic biomass after the liquefaction of the lignocellulosic biomass in a reactor by treatment in hot compressed liquid water (HCW) at sub- and/or super-critical condition, said alkaline liquid being added into the reactor or into process equipment after the reactor, for preventing, minimizing or eliminating clogging and/or fouling of lignin components in process equipment and for quenching the liquefaction of the lignocellulosic biomass. Preferred embodiments of the present invention disclosed above are also valid for the use of an alkaline liquid as an additive to a lignocellulosic biomass after the liquefaction of the lignocellulosic biomass.

Figure 3:
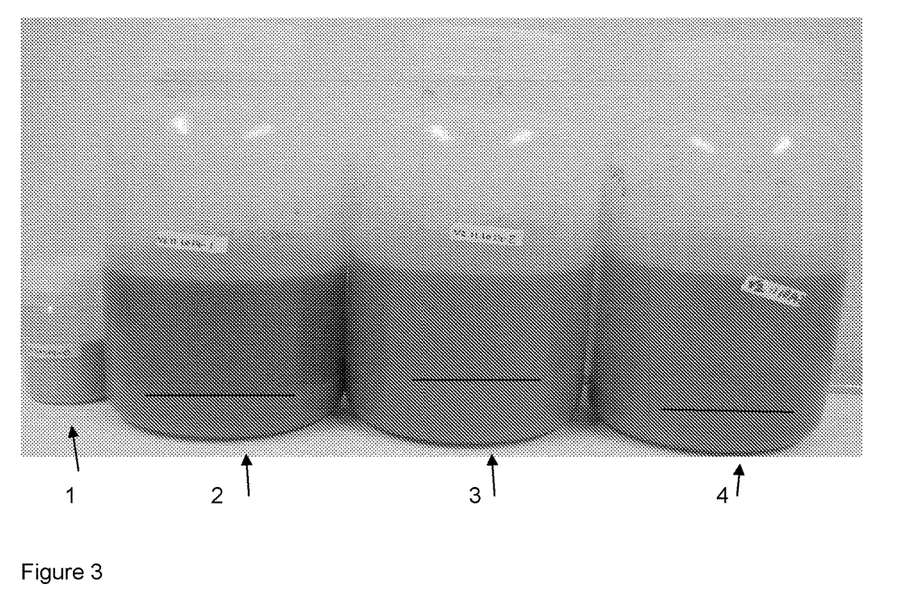
FIG. 3 visually compares (1) feed solution (8% dry matter) with production solution containing various amounts of sodium hydroxide, namely, (2) sodium hydroxide added to process, pH value around 5, (3) no sodium hydroxide added, pH value around 3, and (4) sodium hydroxide added into the process, pH value around 5. Lines indicate the level of sediment.

Examples and Description of FIG. 3

Experiments have been conducted using caustic/alkaline solution, namely sodium hydroxide (aq.), in connection with liquefaction of a lignocellulosic biomass feedstock in HCW at sub-critical conditions. Trials have been performed where the alkaline solution have been added in small amount into the biomass liquid solution (feed) in the reactor or after reactor to increase the solubility of lignin components and to possibly quench the liquefaction. Moreover, other trials have been performed were the alkaline solution has been used to (flush) wash the process system when no feed is in the process system.

The process system comprises inter alia feed tubing for the biomass feed, pre-heater(s), a liquefaction reactor, an injection pump and tubing for feeding the alkaline solution into the process system, and a capillary receiving the product solution after liquefaction, after having been cooled in cooler(s) or by injection of cold water directly into the production solution for quenching. Such subsequent cold water injection may be performed to quench the reaction and to instantly solidify lignin components, instead of using an alkaline solution for the quenching, such as according to what has been said above.

One of the trials was performed to investigate the clogging preventing effect according to the present invention. Sodium hydroxide was in this experiment fed into the system between two pre-heaters. The clogging test was performed with conditions of: set liquefaction temperature 310° C. and a slurry dry matter level of 8%. A sodium hydroxide (25% conc.) was introduced into the process flow, which in turn should give a concentration of about 1.2% sodium hydroxide (aq.) in the process flow (biomass flow, HCW and sodium hydroxide). The fouling or clogging of the pre-heater was evaluated in terms of the temperature difference between the plates and the process flow and the change of this over time. As the temperature difference increased, there was a fouling and the sodium hydroxide flow did not take care of the entire problem. However, when the sodium hydroxide was introduced, the temperature difference decreased, so there seemed to be a very positive effect achieved by the sodium hydroxide. The concentration of the sodium hydroxide in the mixed process flow should, however, be increased somewhat for a total effect. A concentration of 1.5-3% should probably be enough in the mixed process flow for taking care of the fouling problem.

Another trial was performed for evaluation using pulse washing of sodium hydroxide (aq.). This trial, which was performed during somewhat over 3 hours, to test if a good cleaning of the pre-heaters could be achieved using a stronger sodium hydroxide pulse. The test was performed by switching feed from slurry to 3% sodium hydroxide solution every 15 minutes of operation, which pulses lasted up to about 2 minutes of time. Also this clogging was performed with conditions of: set liquefaction temperature 310° C. and a slurry dry matter level of 8%. The test was stopped with no clogging/excessive fouling experienced. The conclusion made was that progressive fouling in the (second) heater was evident between each sodium hydroxide pulse. Sodium hydroxide pulses of 2 min at 3% concentration seemed to be a required level to get total cleaning of the heater surface. Another effective choice is short pulses, 5-15 seconds, with water flushes in between, During the trials, product observations have also been made. In FIG. 3 there is shown different samples. From left to right there is shown, 1) solution in the feed tank (8% dry matter), 2) production solution with sodium hydroxide added into the process, pH value around 5, 3) production solution with no sodium hydroxide added into the process, pH value around 3, and 4) production solution with sodium hydroxide added into the process, pH value around 5, where the process was operated with only one pre-heater activated. Lines have been added into FIG. 3 to clearly show the level of sediment, and as notable, the sample with no pH adjustment, with lowest pH, had also most sediment. This seems to indicate a sample having a larger amount of lignin components in a solid state. It should, however, be noted that also other solid components, like particles etc., besides lignin also may be present in the sediment fraction. Also such particles etc. may create a possible fouling or clogging problem if not removed.

A Fourth Aspect of the Present Invention

According to a fourth aspect of the present invention, there is provided a process for treatment of lignocellulosic biomass at super-critical and/or subcritical conditions.

Different processes for degrading and converting biomass into value-adding compounds are known. Degradation of biomass in sub- or super-critical conditions is known.

WO2011/091044 discloses methods for the continuous treatment of biomass, comprising a pretreatment step, wherein said biomass is contacted with a first supercritical, near-critical, or sub-critical fluid to form a solid matrix and a first liquid fraction; and a hydrolysis step, wherein said solid matrix formed in said pretreatment step is contacted with a second super-critical or near-supercritical fluid to produce a second liquid fraction and an insoluble lignin-containing fraction. According to the process disclosed in WO2011/091044, it is intended to keep the lignin in an insoluble state so that a liquid fraction containing xylose and a solid fraction containing cellulose and lignin may be separated after pre-treatment, such as via skimming or filtration. It is also mentioned that the temperature of the hydrolyzed slurry may be reduced such that the lignin precipitates, possibly without the addition of a precipitation or flocculating agent.

Also WO2011/091044 is related to a different process than the present invention. The process according to WO2011/091044 aims at keeping the lignin in an insoluble state.

Modifications to prior art techniques are needed to improve the efficiency of converting of biomass from renewable resources and/or waste materials to more valuable products and to find new ways to more economically degrade the biomass and turn it into value adding products or intermediates. Thus there is a need to modify the known processes to increase the output of degraded material and lower the costs during processing.

Summary of a Fourth Aspect of the Invention

The fourth aspect of the present invention concerns a process for treatment of lignocellulosic biomass at super-critical and/or subcritical conditions which process aims at liquefying the lignin present in the biomass or bring it into suspension and thereafter remove it together with the formed liquid phase at a separation after the treatment at super-critical and/or subcritical conditions.

The method according to the fourth aspect of the present invention relates to a method for liquefaction of a lignocellulosic biomass feedstock, wherein the biomass feedstock is subjected to a liquefaction by treatment in hot compressed liquid water at subcritical or supercritical conditions, resulting in a liquid and a solid phase, and separating the liquid phase from the solid phase, wherein an additive selected from a dispersing agent and/or a caustic solution is added before the separation is performed.

Alternatively, an oxidizing agent is added before the separation step.

In one embodiment, the method comprises the steps of:
a) loading the biomass feedstock to a reactor;
b) subjecting the biomass feedstock to a liquefaction by treatment in hot compressed liquid water at subcritical and/or supercritical conditions, resulting in a mixture of a liquid phase and a solid phase in said reactor;

c) separating the liquid phase with monomer and/or oligomer sugars, and liquid and/or suspended lignin, to avoid continued detrimental decomposition from the remaining solid phase; and wherein the additive is a dispersing agent and is added before step b), during step b) and/or before step c) is performed; or a caustic solution and is added before step c) is performed.

In another embodiment of the present invention the liquefaction is performed in a temperature of at least 200° C., preferably at 200-300° C.

In yet another embodiment the liquefaction is performed sequentially in at least two steps, and wherein separation of a liquid phase is performed after each step, wherein the temperature in the first step is 200-280° C. and in the second step is 280-400° C. However, the liquefaction may be performed sequentially in at least two separate reactors, and wherein separation of a liquid phase is performed after each reactor.

Another embodiment discloses that the liquefaction is preferably performed at a sub-critical condition implying a temperature of below 374° C.

In one embodiment the liquefaction is performed in a continuous flow system.

In another embodiment the method is performed free from any other added solvents besides HCW.

The fourth aspect of the present invention also relates to the use of a dispersing agent and/or a caustic solution as an additive before a separation of a liquid phase from a solid phase of hot compressed liquid water at subcritical and/or supercritical condition treated lignocellulosic biomass.

The present invention provides an opportunity to remove the lignin present in lignocellulosic biomass as soon as possible in the degradation process. The present invention is thus saving a lot of costs and time for the future processing of the lignocellulosic biomass.

Specific Embodiments of a Fourth Aspect of the Invention

Lignocellulosic biomass mainly consists of hemicelluloses, cellulose and lignin.

Lignocellulosic biomass is degraded by the aid of a liquefaction using hot compressed liquid water (HCW) at subcritical or supercritical conditions. Improved degradation and a high content of resulting monomers and oligomers are obtained by the method according to the fourth aspect of the present invention that includes use of dispersing agents and/or caustic solutions. The addition of dispersing agents and/or caustic solutions makes the lignin in the thermally treated mixture to become less intertwined with the cellulose present. The lignin is obtained in liquid form or as a suspension in the formed liquid fraction after the liquefaction. In this condition the lignin may be separated from the remaining cellulosic material and be removed together with the degraded hemicellulosic material in water solution at the separation. Thereafter lignin may be separated from the water solution containing the degradation products from the hemicellulose and be further processed.

Lignocellulosic biomass may be degraded in sequential steps. By subjecting lignocellulosic biomass to hot compressed liquid water (HCW) at subcritical or supercritical conditions in different steps the total amount of resulting monomers and oligomers obtained may be increased. Preferably the sequential steps have an increasing temperature for each step of the treatment. Hot compressed liquid water at subcritical and/or supercritical conditions may be injected where the reaction takes place, e.g. a reactor, creating conditions subcritical and/or supercritical conditions in the reactor, or water present in such a reactor may be brought up to subcritical and/or supercritical conditions resulting in hot compressed liquid water.

After a first liquefaction the water soluble and liquid materials may be separated from the remaining solids. Before the separation is made it is important that the mixture is brought in contact with at least one additive chosen from a dispersing agent and a caustic solution, or a combination thereof. In the fraction with the water soluble and liquid materials removed from the solids there are the monomers and oligomers of sugars obtained from the degradation of the biomass but also lignin in liquid form or as a suspension in the monomers and oligomers of sugars in water. The addition of the additive, i.e. the dispersing agent and/or caustic solution, must be made before the separation process. However, the additive may be added at different stages of the total process, and may be added at more than one stage, but the important thing is that if not added before it must at least be added right before the separation.

The remaining solids after the first liquefaction may then be subjected to further liquefactions. A second liquefaction is then preferably preformed at a higher temperature.

As notable from above, the liquefaction may be performed in "sub- and/or super-critical condition" which implies that both of these conditions are possible as well as a combination where one first liquefaction step first may be performed in e.g. a sub-critical condition and a second liquefaction step may be performed in e.g. a super-critical condition. In relation to the above stated it should be mentioned that the liquefaction according to the present invention preferably is performed in a sub-critical condition for HCW, but above 200° C. Therefore, according to one specific embodiment of the present invention, the liquefaction is performed in a temperature of at least 200° C.

For dissolving hemicellulose effectively, the temperature should preferably be held at least 200° C., preferably at least 230° C., preferably at least 250° C. As such these temperatures may be seen as preferred minimum levels for the liquefaction according to the present invention.

For dissolving cellulose, the temperature should be at least 280° C. Therefore, according to one specific embodiment of the present invention the liquefaction is performed in a temperature of at least 280° C. Also the reaction time is an important parameter. According to the present invention, the reaction time should be held short, irrespective if e.g. a semi-batch or a continuous flow system is used for the liquefaction. A reaction time, i.e. a time where the temperature is held at the intended minimum during liquefaction, of below one minute is preferred according to the present invention.

As mentioned above, preferably the liquefaction is performed at a sub-critical condition for the HCW, which implies a temperature of below 374° C. A preferred range for the liquefaction, when aiming for the cellulose liquefaction, is a temperature range of 280-370° C.

The process according to the present invention is preferably performed in a continuous flow system, such as in a tube, possibly intended for pre-treatment and liquefaction. However, also separate units may be used, depending on the aim of the liquefaction. For example, according to one specific embodiment of the present invention, the liquefaction is performed sequentially in at least two "separate" reactors, and wherein separation of a liquid phase is performed after each reactor. This may be performed by e.g. feeding a biomass slurry into a first continuous flow reactor in which part of the biomass is liquefied, such as e.g. the hemicelluloses, then separating a first liquid phase solution, thereafter feeding the biomass slurry containing the solid material into a second continuous flow reactor in which at least part of the remaining biomass is liquefied, and finally separating a second liquid phase solution, and hence water and water soluble components, from the optionally remaining biomass slurry being discharged from said second flow reactor. Moreover, although the flow reactors are mentioned as separate reactors, they may also be different parts of one and the same tube reactor having different portions for different liquefactions and separations and so forth. As understood from above, the method according to the present invention may also comprise removal of non-solubilised material, and also comprise the reprocessing of such removed non-solubilised material.

According to one embodiment a first step is preferably performed to bring forth the hemicellulose of the lignocellulosic biomass and degrade that into monomers and oligomers. At that same first step the temperature should be high enough to make the lignin more mobile in the biomass structure and make the lignin less intertwined with the remaining biomass material. The lignin is preferably separated from the remaining components in the solid phase it previously was attached to in the biomass. Thus, one may say that the lignin preferably becomes a liquid or is in a suspended state after the first liquefaction. The liquid and/or suspended lignin is in the following considered to belong to the water soluble and liquid materials of this first liquefaction and separation. The temperature of this first liquefaction is between 200 and 280° C. For example the lower temperature of the range may be 220, 230, 240 or 250° C. Preferably the temperature is in the range 240-260° C. or 250-280° C. The reaction time for the liquefaction is below 1 minute, e.g. in the range 1 to 45 seconds, 1.5 to 30 seconds, or 1.5 to 15 seconds. The conditions of the thermal treatment are within the subcritical range. However, hot compressed liquid water (HCW) at subcritical or supercritical conditions may be injected into the reactor containing the lignocellulosic biomass. If HCW at supercritical condition is injected in to the reactor, the degradation of the biomass takes place at subcritical conditions due to a decrease in temperature when brought into the reactor.

After a first liquefaction the water soluble and liquid materials are separated from the remaining solids. This separation may be performed by decantation, centrifugation and/or filtration. The separation step is performed at a temperature of 20-280° C., e.g. 200-280° C. or 210-250° C. In the fraction of the water soluble and liquid materials removed from the solids there are the monomers and oligomers of sugars obtained from the degradation of hemicelluloses and also the liberated, liquid lignin. The lignin present in the sugar solution is in the form of an emulsion or dispersion depending on the temperature and thus the state of the lignin. The lignin mentioned in this application refers to both lignin components and lignin derivatives. The obtained emulsion or dispersion of lignin in the sugar solution may be further processed to separate the lignin from the sugar solution. The separated lignin may then be used as a component for other processes.

The remaining solids after the first liquefaction may be subjected to a further liquefaction. This second liquefaction is then performed at a higher temperature to convert the remaining cellulose of the used lignocellulosic biomass into monomers and oligomers. By subjecting the remaining solids to hot compressed liquid water (HCW) at subcritical or supercritical conditions monomers and oligomers are obtained from the degradation of cellulose. The temperature of this second liquefaction is between 280 and 400° C. For example the temperature range may be 280-380° C., 280-370° C., 290-360° C., 300-360° C., 300-350° C. or 320-350° C. The reaction time for the second liquefaction is also below 1 minute, e.g. in the range 1 to 45 seconds, 1.5 to 30 seconds, or 1.5 to 15 seconds.

After this second liquefaction, if there are any remaining solid materials, the water soluble and liquid materials are separated from the remaining solids. Such a separation may be performed by decantation, centrifugation and/or filtration. The separation step may be performed at a temperature of 20-400° C., e.g. 200-400° C. or 210-300° C.

Dispersing agents may be added to the degradation process of the lignocellulosic biomass. The dispersing agents may be added to the biomass feed before any thermal treatment, to the hot compressed liquid water which then is brought in contact with the biomass feed during the first liquefaction, or to the thermally treated biomass i.e. after the first liquefaction but before the separation step. The dispersing agents should preferably be dispersed throughout the material to which it is added. The dispersing of the dispersing agents may be done by mixing. The dispersing agents aid the liberation of the lignin from the structure it was previously locked in before the thermal treatment, making the lignin not as intertwined in the cellulose, as it used to be, and may assist in the formation of an emulsion or dispersion of the lignin in the formed sugar solution. Examples of dispersing agents are lignosulphonates, polyacrylates, sulphonates, carboxylates, salts of lecithin, and SASMAC (a co-polymer of a sulphonated acrylate and maleic acid). Preferred lignosulphonates are ammonium lignosulphonate, sodium lignosulphonate, calcium lignosulphonate, magnesium lignosulphonate, and ferrochrome lignosulphonate. Preferred polyacrylates are sodium, potassium, lithium and ammonium polyacrylates. Typical acrylate monomers used to form acrylate polymers are acrylic acid, methacrylate, acrylonitrile, methyl acrylate, ethyl acrylate, 2-chloroethyl vinyl ether, 2-ethylhexyl acrylate, hydroxyethyl methacrylate, butyl acrylate, butyl methacrylate, and TMPTA.

Caustic solution may be added to the degradation process of the lignocellulosic biomass after the first thermal treatment but before the separation step. Preferably sodium hydroxide and/or potassium hydroxide are used as caustic solution. The caustic solution is thoroughly mixed with the thermally treated materials. By the addition of caustic solution also a basic pH may be obtained. The caustic solution act to make the lignin less intertwined in the cellulose and to make it more liberated, possibly liquid. The liberated lignin is then in liquid form following the liquid phase at the first separation step.

By the use of caustic solution and/or dispersing agents in the process of the present invention, the liquid phase after the first separation step contains sugar monomers and oligomers, and lignin in water. The lignin may later be separated from the monomer and oligomer sugar solution. The remaining solid cellulose is processed thermally in another liquefaction process to obtain more monomer and oligomer sugar solution, and optionally some remaining solids. The two fractions of monomer and oligomer sugar solutions, from the first and second liquefaction, may be combined and processed further. In this way the material going through the second liquefaction is of a considerable lower amount compared to if lignin would have been present in the second step. This is very economical for the overall process. Also, the lignin is not present in the second stage and may not influence the reaction in a negative way.

Oxidizing agents may also be added to the process of the present invention before the separation of liquids comprising lignin from solids. The addition of such oxidizing agents may be made before, during or after a liquefaction. Preferably the oxidizing agents used are oxygen, air and hydrogen peroxide, or any combination thereof. The addition of oxidizing agents may be made to increase the solubility of lignin or other components.

According to one specific embodiment of the present invention, the liquefaction is performed in hot compressed liquid water (HCW) at a sub- and/or super-critical condition. It should be said that the liquefaction may also be performed in mixtures at a sub- and/or super-critical condition, for instance in a mixture of HCW together with amounts of acids, carbon dioxide or ethanol. To use HCW, optionally with addition of some acid(s), is however preferred as the solvent for the liquefaction according to the present invention.

As hinted above, the process according to the present invention is preferably performed in a continuous flow system, such as a tube, however the principle may also be used for batch or semi-batch systems. Also processes in such systems are embodied by the present invention.

As understood from above, but also now clearly stated, any of the first to fourth aspects of the present invention, and any embodiments specified in relation thereto, may be combined with another aspect or specific embodiment thereof of the present invention.

The invention claimed is:

1. A method for treatment of a biomass feedstock comprising
    subjecting the biomass feedstock to liquefaction, by treatment with hot compressed liquid water (HCW) at a subcritical condition;
    wherein the liquefaction is carried out
        at a temperature of from 330° C. to below 374° C.,
        at a pH below 3.0, and
        for a reaction time below 1 minute.

2. A method according to claim 1, also comprising subjecting the biomass feedstock to a subsequent quenching step.

3. A method according to claim 2, wherein the quenching step is made to avoid continued detrimental decomposition, and wherein the quenching is performed by injection of water into a monomer and/or oligomer sugar mixture solution produced after the treatment with hot compressed liquid water (HCW) at subcritical conditions, for a rapid cooling of the solution so that liquid lignin components or liquid lignin derivative components are solidified.

4. A method according to claim 3, wherein the liquid lignin components or liquid lignin derivative components are solidified into particles.

5. A method according to claim 3, wherein the produced solid lignin components or lignin derivative components are separated.

6. A method according to claim 2, wherein the quenching is performed by injection of water into the monomer and/or oligomer sugar mixture solution to a post-quenching temperature below 165° C.

7. A method according to claim 6, wherein the quenching is performed so that the post-quenching temperature is reached within a time of maximum 10 seconds.

8. A method according to claim 7, wherein the post-quenching temperature is reached within a time of maximum 2 seconds.

9. A method according to claim 2, wherein the quenching is performed by injection of water into the monomer and/or oligomer sugar mixture solution to a post-quenching temperature below 150° C.

10. The method according to claim 1, wherein inorganic and/or organic acids are added to the biomass feedstock before and/or during the liquefaction.

11. The method according to claim 10, wherein the inorganic acids are chosen from sulfuric acid, sulfonic acid, phosphoric acid, phosphonic acid, nitric acid, nitrous acid, hydrochloric acid, hydrofluoric acid, hydrobromic acid, and hydroiodic acid, or any combination.

12. The method according to claim 10, wherein the organic acids are chosen from aliphatic carboxylic acids, aromatic carboxylic acids, dicarboxylic acids, aliphatic fatty acids, aromatic fatty acids, and amino acids, or any combination.

13. The method according to claim 1, wherein the liquefaction is performed sequentially in at least two separate reactors, and wherein separation of a liquid phase is performed after each reactor.

14. A method according to claim 13, also comprising a step wherein an additive selected from a dispersing agent and/or a caustic solution is added to the treated biomass feedstock before a separation of a liquid phase from a solid phase is performed.

15. The method according to claim 14, wherein the caustic solution is chosen from sodium hydroxide or potassium hydroxide, or a combination.

16. The method according to claim 14, wherein the dispersing agent is chosen from lignosulphonates, polyacrylates, sulphonates, carboxylates, salts of lecithin, and sodium allyl sulphonate/maleic acid copolymer (SASMAC).

17. The method according to claim 16, wherein the lignosulphonates are chosen from ammonium lignosulphonate, sodium lignosulphonate, calcium lignosulphonate, magnesium lignosulphonate, and ferrochrome lignosulphonate, or any combination thereof.

18. The method according to claim 16, wherein the polyacrylates are chosen from sodium, potassium, lithium and ammonium polyacrylates, or any combination thereof.

19. The method according to claim 16, wherein the polyacrylates are chosen from polymers formed from the monomers acrylic acid, methacrylate, acrylonitrile, methyl acrylate, ethyl acrylate, 2-chloroethyl vinyl ether, 2-ethylhexyl acrylate, hydroxyethyl methacrylate, butyl acrylate, butyl methacrylate, or trimethylolpropane triacrylate (TMPTA), or any combination thereof.

20. The method according to claim 1, wherein the liquefaction is performed in a continuous flow system.

21. The method according to claim 1, wherein the method is performed free from any other added solvents besides HCW.

22. The method according to claim 1, wherein the pH value is increased during and/or after the liquefaction to slow down or quench the liquefaction reaction by the use of a base.

23. The method according to claim 1, wherein the reaction time of the liquefaction is set to between 1 and 45 seconds.

24. A method according to claim 1, wherein the method also comprises removal of any material not solubilized.

25. A method according to claim 1, also comprising a step for preventing, minimizing or eliminating clogging and/or fouling of sticky biomass components in process equipment, wherein an alkaline liquid is washed through the process equipment, either as a sole solution between regular process operations of a biomass process flow in a liquid solution, or as added directly into the liquid solution for dissolving biomass components which are or otherwise may become sticky.

26. A method according to claim 25, wherein the alkaline liquid is processed separately from the biomass process flow solution after the washing or the addition thereof.

27. A method according to claims 25, wherein the alkaline liquid is recovered after the washing or addition thereof, for further washing or addition.

28. A method according to claim 25, wherein the alkaline liquid is a liquid based on caustic liquor or ammonia.

29. A method according to claim 25, wherein an oxidizing agent also is added in the alkaline liquid.

* * * * *